US009823401B2

United States Patent
Goto et al.

(10) Patent No.: US 9,823,401 B2
(45) Date of Patent: Nov. 21, 2017

(54) CURED FILM FORMATION COMPOSITION, ORIENTATION MATERIAL, AND RETARDATION MATERIAL

(71) Applicant: NISSAN CHEMICAL INDUSTRIES, LTD., Tokyo (JP)

(72) Inventors: Kohei Goto, Funabashi (JP); Shojiro Yukawa, Funabashi (JP); Masato Moriuchi, Funabashi (JP); Tadashi Hatanaka, Funabashi (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 0 days.

(21) Appl. No.: 15/183,350

(22) Filed: Jun. 15, 2016

(65) Prior Publication Data

US 2016/0291412 A1    Oct. 6, 2016

Related U.S. Application Data

(63) Continuation of application No. 14/773,563, filed as application No. PCT/JP2014/055814 on Mar. 6, 2014, now Pat. No. 9,529,132.

(30) Foreign Application Priority Data

Mar. 8, 2013 (JP) .................................. 2013-047155
May 7, 2013 (JP) .................................. 2013-097877

(51) Int. Cl.

| | | |
|---|---|---|
| F21V 9/14 | (2006.01) | |
| G02B 5/30 | (2006.01) | |
| G02C 7/12 | (2006.01) | |
| G02B 5/32 | (2006.01) | |
| C09D 133/04 | (2006.01) | |
| C09D 167/02 | (2006.01) | |
| C07C 69/738 | (2006.01) | |
| G02F 1/1337 | (2006.01) | |
| G02B 1/04 | (2006.01) | |
| C09D 133/12 | (2006.01) | |
| C09D 133/14 | (2006.01) | |
| C09K 19/56 | (2006.01) | |
| C08F 2/48 | (2006.01) | |
| C08K 5/134 | (2006.01) | |
| C08L 61/28 | (2006.01) | |
| G02F 1/13363 | (2006.01) | |

(Continued)

(52) U.S. Cl.
CPC .............. *G02B 5/32* (2013.01); *C07C 69/738* (2013.01); *C09D 133/04* (2013.01); *C09D 133/12* (2013.01); *C09D 133/14* (2013.01); *C09D 167/02* (2013.01); *C09K 19/56* (2013.01); *G02B 1/04* (2013.01); *G02F 1/133711* (2013.01); *G02F 1/133753* (2013.01); *G02F 1/133788* (2013.01); *C08K 5/101* (2013.01); *C08K 5/1345* (2013.01); *C08K 5/20* (2013.01); *C08L 61/28* (2013.01); *G02F 2001/133633* (2013.01); *G02F 2001/133757* (2013.01)

(58) Field of Classification Search
CPC ......... G02F 1/133711; G02F 1/133753; G02F 1/133788; G02F 2001/133757; C09K 19/56; C09K 133/12; C09K 133/14; C08K 5/101
USPC ............................. 252/585; 522/69; 560/52
See application file for complete search history.

(56) References Cited

U.S. PATENT DOCUMENTS

2015/0191572 A1* 7/2015 Hatanaka ................ C08L 33/24
522/69

FOREIGN PATENT DOCUMENTS

| | | |
|---|---|---|
| JP | H10232365 A | 9/1998 |
| JP | 2001-517719 A | 10/2001 |
| JP | 3611342 B2 | 1/2005 |

(Continued)

OTHER PUBLICATIONS

Brooks, Tracy et al. "Taxane-based reversal agents modulate drug resistance mediated by P-glycoprotein, multidrug resistance protein, and breast cancer resistance protein," Molecular Cancer Therapeuticws, vol. 2, No. 11, pp. 1195-1205, 2003.

(Continued)

*Primary Examiner* — Bijan Ahvazi
(74) *Attorney, Agent, or Firm* — Oliff PLC

(57) ABSTRACT

A cured-film formation composition that includes: (A) one or more compounds having a photo-aligning group and hydroxy group, etc.; (B) a polymer having at least one substituent from the group of a hydroxy group, carboxy group, amino group, and alkoxysilyl group, and the like; and (C) a cross-linking agent. Component (A) contains a compound having a group of Formula [1] below as the photo-aligning group:

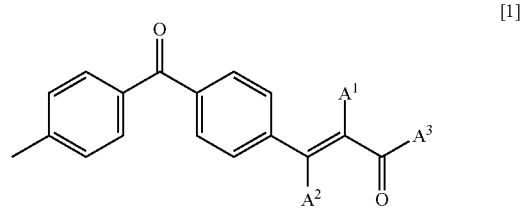

[1]

where $A^1$ and $A^2$ are independently a hydrogen atom or methyl group; and $A^3$ is a hydroxy group. A cured-film is formed from the cured-film formation composition, and orientation material is formed by use of photo-alignment technique. A retardation material is obtained by applying a polymerizable liquid crystal on the orientation material and curing it.

7 Claims, No Drawings

(51) Int. Cl.
  *C08K 5/20* (2006.01)
  *C08K 5/101* (2006.01)

(56) References Cited

FOREIGN PATENT DOCUMENTS

| | | |
|---|---|---|
| JP | 2005-049865 A | 2/2005 |
| JP | 2009-058584 A | 3/2009 |
| WO | 2011/126019 A1 | 10/2011 |
| WO | 2011/126021 A1 | 10/2011 |
| WO | 2011/126022 A1 | 10/2011 |
| WO | 2013/054784 A1 | 4/2013 |
| WO | 2013/146469 A1 | 10/2013 |
| WO | 2014/010688 A1 | 1/2014 |
| WO | 2014/042216 A1 | 3/2014 |
| WO | 2014/065324 A1 | 5/2014 |
| WO | 2014/073658 A1 | 5/2014 |

OTHER PUBLICATIONS

Ojima, Iwao et al. "Design, Synthese and Structure-Activity Relationships of Novel Taxane-Based Multidrup Resistance Reversal Agents," Journal of Medical Chemistry, vol. 48, No. 6, pp. 2218-2228, 2005.

Huang, Qing et al. "Targeting FtsZ for Antituberculosis Drug Discovery: Noncytotoxic Taxanes as Novel Antituberculosis Agents," Journal of Medical Chemistry, vol. 49, No. 2, pp. 463-466, 2006.

Salem, Ola I. A. et al. "Novel 5a-Reductase Inhibitors: Synthesis, Structure-Activity Studies, and Pharmacokinetic Profile of Phenoxybenzoylphenyl Acetic Acids," Journal of Medical Chemistry, vol. 49, No. 2, pp. 748-759, 2006.

Jun. 10, 2014 Search Report issued in International Patent Application No. PCT/JP2014/055814.

Jun. 10, 2014 Written Opinion issued in International Patent Application No. PCT/JP2014/055814.

* cited by examiner

CURED FILM FORMATION COMPOSITION, ORIENTATION MATERIAL, AND RETARDATION MATERIAL

CROSS-REFERENCE TO PRIOR APPLICATIONS

This is a continuation of application Ser. No. 14/773,563 filed Sep. 8, 2015, which a National Stage Application of PCT/JP2014/055814 filed Mar. 6, 2014, and claims the benefit of Japanese Application Nos. 2013-047155 filed Mar. 8, 2013 and 2013-097877 filed May 7, 2013. The entire disclosures of the prior applications are hereby incorporated by reference herein in their entirety.

TECHNICAL FIELD

The present invention relates to a cured-film formation composition, an orientation material, and a retardation material.

BACKGROUND ART

Recently, in the field of displays such as televisions including liquid crystal panels, 3D displays with which 3D images can be enjoyed have been developed to achieve high performance. In such 3D displays, a stereoscopic image can be displayed by, for example, making the right eye of a viewer see an image for the right eye and making the left eye of the viewer see an image for the left eye.

Various 3D display methods for displaying 3D images can be used, and examples of the methods known as methods requiring no special eyeglasses include a lenticular lens method and a parallax barrier method.

As one of display methods for viewers to see 3D images with eyeglasses, a circularly polarized glasses method, for example, is known (see Patent Document 1, for example).

In a 3D display using the circularly polarized light glasses method, a retardation material is generally arranged on a display element for forming an image of a liquid crystal panel and the like. In this retardation material, two retardation regions having different retardation characteristics are regularly arranged each in plurality to constitute a retardation member that is patterned. In the present specification, a retardation member thus patterned in which a plurality of retardation regions having different retardation characteristics are arranged is called a patterned retardation material hereinafter.

The patterned retardation material can be fabricated by optically patterning a retardation substance including a polymerizable liquid crystal as disclosed in Patent Document 2, for example. In the optical patterning of the retardation substance including a polymerizable liquid crystal, a photo-alignment technique known for forming an orientation material for a liquid crystal panel is used. More specifically, a coating made of a material having photo-alignment properties is provided on a substrate, and two kinds of polarized beams having different polarization directions are radiated on this coating. Thus, a photo-alignment film is obtained as an orientation material in which two kinds of liquid crystal alignment regions are formed and the directions of alignment control of liquid crystals in the regions are different. Onto this photo-alignment film, a retardation substance containing a polymerizable liquid crystal in a solution state is applied to perform alignment of the polymerizable liquid crystal. Subsequently, the polymerizable liquid crystal thus aligned is cured to form a patterned retardation material.

As materials having photo-alignment properties that can be used in orientation material formation using a photo-alignment technique for liquid crystal panels, an acrylic resin and a polyimide resin, for example, are known that have in a side chain thereof a photodimerized moiety such as a cinnamoyl group and a chalcone group, for example. It is disclosed that these resins exhibit a property of controlling alignment of liquid crystals (hereinafter, also called liquid crystal alignment properties) by polarized UV irradiation (see Patent Document 3 to Patent Document 5).

PRIOR-ART DOCUMENTS

Patent Documents

Patent Document 1: Japanese Patent Application Publication No. H10-232365 (JP H10-232365 A)
Patent Document 2: Japanese Patent Application Publication No. 2005-49865 (JP 2005-49865 A)
Patent Document 3: Japanese Patent No. 3611342 (JP 3611342 B2)
Patent Document 4: Japanese Patent Application Publication No. 2009-058584 (JP 2009-058584 A)
Patent Document 5: Published Japanese Translation of PCT Application No. 2001-517719 (JP 2001-517719 A)

SUMMARY OF THE INVENTION

Problem to be Solved by the Invention

As described above, the patterned retardation material is formed by laminating a layer of a cured polymerizable liquid crystal on a photo-alignment film being an orientation material. The patterned retardation material having such a laminate structure can be used to constitute a 3D display, in the laminated state as such.

Accordingly, a cured film that can be used as an orientation material excellent in both liquid-crystal alignment properties and light transmission properties, and a cured-film formation composition for forming the cured film need to be developed.

The present invention has been made based on the above-described findings and study results. An object of the present invention is to provide a cured-film formation composition that is suitable to form a cured film having excellent liquid-crystal alignment properties and excellent light transmission properties. In particular, an object of the present invention is to provide a cured-film formation composition that forms a cured film exhibiting excellent liquid-crystal alignment properties and excellent light transmission properties when the cured-film formation composition is used as an orientation material and a layer of a polymerizable liquid crystal is arranged thereon.

An object of the present invention is to provide an orientation material excellent in liquid-crystal alignment properties and light transmission properties.

An object of the present invention is to provide a retardation material that can be optically patterned with high precision.

Other objects and advantages of the present invention will be apparent from the following description.

Means for Solving the Problem

A first aspect of the present invention relates to a cured-film formation composition comprising:

a component (A) that is one or more compounds having a photo-aligning group and one group selected from the group consisting of a hydroxy group, a carboxy group, an amino group, and an alkoxysilyl group;

a component (B) that is at least one polymer selected from a component (B-1): a polymer that has at least one substituent selected from the group consisting of a hydroxy group, a carboxy group, an amino group, and an alkoxysilyl group, a component (B-2): a polymer that has a substituent capable of thermally reacting with the component (A) and is self-cross-linkable, and a component (B-3): a melamine formaldehyde resin; and a component (C) that is a cross-linking agent (when the component (B) is the component (B-2), the component (C) is optionally the same as the component (B-2)), in which the component (A) contains at least a compound having a group of Formula [1] below as the photo-aligning group.

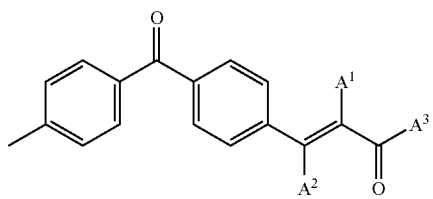

[1]

(In the Formula, $A^1$ and $A^2$ are independently a hydrogen atom or a methyl group; and $A^3$ is a hydroxy group, a mercapto group, an amino group, a $C_{1-10}$ alkoxy group, a $C_{1-10}$ alkylthio group, a $C_{1-10}$ alkylamino group, a phenoxy group, a phenylthio group, a phenyl amino group, a biphenyl amino group, a phenyl group, or a biphenyl group; and hydrogen atoms on the phenylene group and on the phenyl group are independently and optionally substituted with at least one substituent selected from a $C_{1-10}$ alkyl group, a $C_{1-10}$ alkoxy group, a halogen atom, a cyano group, and a nitro group.)

In the first aspect of the present invention, the compound of the component (A) is preferably a compound having a photo-aligning group and a hydroxy group.

In the first aspect of the present invention, the cured-film formation composition preferably includes a compound (D) having a hydroxy group and an acrylic group, other than the component (A).

In the first aspect of the present invention, the cured-film formation composition preferably includes a cross-linking catalyst (E).

A second aspect of the present invention relates to an orientation material characterized by being formed of the cured-film formation composition of the first aspect of the present invention.

A third aspect of the present invention relates to a retardation material characterized by including a cured film that is obtained from the cured-film formation composition of the first aspect of the present invention.

Effects of the Invention

According to the first aspect of the present invention, it is possible to provide a cured-film formation composition suitable for forming a cured film having excellent liquid crystal alignment properties and light transmission properties.

According to the second aspect of the present invention, it is possible to provide an orientation material that has excellent liquid crystal alignment properties and light transmission properties.

According to the third aspect of the present invention, it is possible to provide a retardation material that can be optically patterned with high precision.

According to the present invention, it is possible to provide a compound having a group of Formula [1] below and one group selected from the group consisting of a hydroxy group, a carboxy group, an amino group, and an alkoxysilyl group.

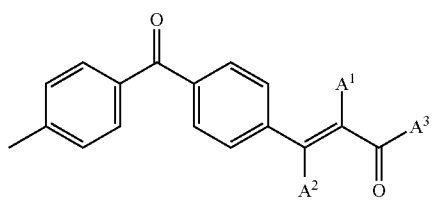

[1]

(In the Formula, $A^1$ and $A^2$ are independently a hydrogen atom or a methyl group; and $A^3$ is a hydroxy group, a mercapto group, an amino group, a $C_{1-10}$ alkoxy group, a $C_{1-10}$ alkylthio group, a $C_{1-10}$ alkylamino group, a phenoxy group, a phenylthio group, a phenyl amino group, a biphenyl amino group, a phenyl group, or a biphenyl group; in which hydrogen atoms on the phenylene group and on the phenyl group are independently and optionally substituted with at least one substituent selected from a $C_{1-10}$ alkyl group, a $C_{1-10}$ alkoxy group, a halogen atom, a cyano group, and a nitro group.)

According to the present invention, it is possible to provide a compound of Formula [2]:

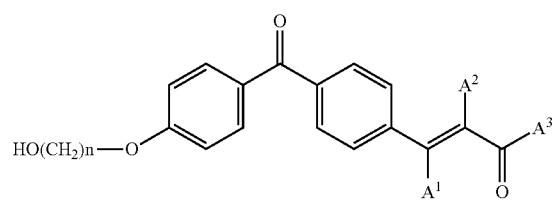

[2]

(In Formula [2], $A^1$ and $A^2$ are independently a hydrogen atom or a methyl group;

$A^3$ is a hydroxy group, a mercapto group, an amino group, a $C_{1-10}$ alkoxy group, a $C_{1-10}$ alkylthio group, a $C_{1-10}$ alkylamino group, a phenoxy group, a phenylthio group, a phenyl amino group, a biphenyl amino group, a phenyl group, or a biphenyl group, in which hydrogen atoms on the phenylene group and on the phenyl group are independently and optionally substituted with at least one substituent selected from a $C_{1-10}$ alkyl group, a $C_{1-10}$ alkoxy group, a halogen atom, a cyano group, and a nitro group; and n is an integer of 2 to 20.)

MODES FOR CARRYING OUT THE INVENTION

A cured-film formation composition (hereinafter, also called "present invention composition") of the present invention will be described hereinafter in detail with reference to specific examples of components and the like. In addition, the following describes a cured film and an orientation material of the present invention using the cured-film formation composition of the present invention, and also a retardation material, a liquid crystal display element, and the like that are formed by using the orientation material.

[Component (A)]

A component (A) of the composition of the present invention is a low-molecular alignment component. The component (A) is a component that imparts photo-alignment properties to a cured film of the present embodiment obtained from the composition of the present invention, and is a photo-alignment component having a lower molecule weight than that of a polymer of a component (B) described below as a base.

In the composition of the present invention, this low-molecular alignment component as the component (A) can be a compound having a photo-aligning group and one group selected from the group consisting of a hydroxy group, a carboxy group, an amino group, and an alkoxysilyl group.

In the present invention, the photo-aligning group is a functional group of a structural moiety to be photodimerized or photoisomerized.

The structural moiety to be photodimerized that the compound of the component (A) can have as the photo-aligning group is a moiety that forms a dimer by irradiation with light, and specific examples thereof include a cinnamoyl group, a chalcone group, a coumarin group, and an anthracene group. Among them, a cinnamoyl group is preferred in terms of having high transparency in the visible light range and high photodimerization reactivity.

In addition, the structural moiety to be photoisomerized that the compound of the component (A) can have as the photo-aligning group is a structural moiety that is converted into a cis form or a trans form by irradiation with light, and specific examples thereof include a moiety containing an azobenzene structure and a moiety containing a stilbene structure. Among them, in terms of high reactivity, the azobenzene structure is preferred.

The compound having a photo-aligning group and one group selected from the group consisting of a hydroxy group, a carboxy group, an amino group, and an alkoxysilyl group is, for example, a compound of Formulae below. Specific examples of such a monomer include Formulae [A1] to [A5]:

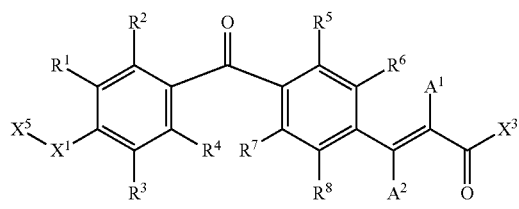

[A1]

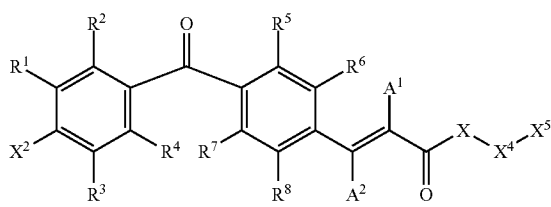

[A2]

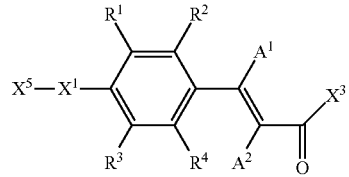

[A3]

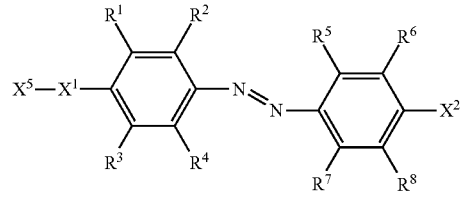

[A4]

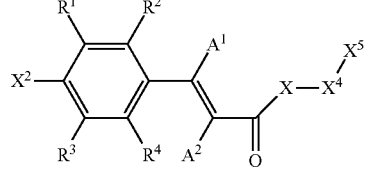

[A5]

In the Formulae, $A^1$ and $A^2$ are independently a hydrogen atom or a methyl group; and $X^1$ is a structure in which one to three groups selected from a $C_{1-18}$ alkylene group, a phenylene group, a biphenylene group, and combinations thereof are bonded through one or more bonds selected from a single bond, an ether bond, an ester bond, an amide bond, an urethane bond, an amino bond, and combinations thereof. $X^2$ is a hydrogen atom, a halogen atom, a cyano group, a $C_{1-18}$ alkyl group, a phenyl group, a biphenyl group, or a cyclohexyl group. In this case, the $C_{1-18}$ alkyl group, the phenyl group, the biphenyl group, and the cyclohexyl group may be bonded through a covalent bond, an ether bond, an ester bond, an amide bond, or a urea bond. $X^3$ is a hydroxy group, a mercapto group, an amino group, a $C_{1-10}$ alkoxy group, a $C_{1-10}$ alkylthio group, a $C_{1-10}$ alkylamino group, a phenoxy group, a phenylthio group, a phenyl amino group, a biphenyl amino group, a phenyl group, or a biphenyl group. $X^4$ is independently a single bond, a $C_{1-20}$ alkylene group, an aromatic-ring group, or an alicyclic group. The $C_{1-20}$ alkylene group may be branched or linear. $X^5$ is a hydroxy group, a carboxy group, an amino group, or an alkoxysilyl group. X is a single bond, an oxygen atom, or a sulfur atom. In these substituents, hydrogen atoms on the phenyl group, on the biphenyl group, on the phenylene group, and on the biphenylene group may be substituted with one or more substituents that are the same or different from each other selected from a $C_{1-4}$ alkyl group, a $C_{1-4}$ alkoxy group, a halogen atom, a trifluoromethyl group, and a cyano group.

In the Formulae, $R^1$, $R^2$, $R^3$, $R^4$, $R^5$, $R^6$, $R^7$, and $R^8$ independently ndependently a hydrogen atom, a $C_{1-4}$ alkyl group, a $C_{1-4}$ alkoxy group, a halogen atom, a trifluoromethyl group, or a cyano group.

Specific examples of the compound having a photo-aligning group and a hydroxy group that is the component (A) include 4-(8-hydroxyoctyloxy)cinnamic acid methyl ester, 4-(6-hydroxyhexyloxy)cinnamic acid methyl ester, 4-(4-hydroxybutyloxy)cinnamic acid methyl ester, 4-(3-hydroxypropyloxy)cinnamic acid methyl ester, 4-(2-hydroxyethyloxy)cinnamic acid methyl ester, 4-hydroxymethyloxycinnamic acid methyl ester, 4-hydroxycinnamic acid methyl ester, 4-(8-hydroxyoctyloxy)cinnamic acid ethyl ester, 4-(6-hydroxyhexyloxy)cinnamic acid ethyl ester, 4-(4-hydroxybutyloxy)cinnamic acid ethyl ester, 4-(3-hydroxypropyloxy)cinnamic acid ethyl ester, 4-(2-hydroxyethyloxy)cinnamic acid ethyl ester, 4-hydroxymethyloxycinnamic acid ethyl ester, 4-hydroxycinnamic acid ethyl ester, 4-(8-hydroxyoctyloxy)cinnamic acid phenyl ester, 4-(6-hydroxyhexyloxy)cinnamic acid phenyl ester, 4-(4-hydroxybutyloxy)cinnamic acid phenyl ester, 4-(3-hydroxypropyloxy)cinnamic acid phenyl ester, 4-(2-hydroxyethyloxy)cinnamic acid phenyl ester, 4-hydroxymethyloxycinnamic acid phenyl ester, 4-hydroxycinnamic acid phenyl ester, 4-(8-hydroxyoctyloxy)cinnamic acid biphenyl ester, 4-(6-hydroxyhexyloxy)cinnamic acid biphenyl ester, 4-(4-hydroxybutyloxy)cinnamic acid biphenyl ester, 4-(3-hydroxypropyloxy)cinnamic acid biphenyl ester, 4-(2-hydroxyethyloxy)cinnamic acid biphenyl ester, 4-hydroxymethyloxycinnamic acid biphenyl ester, 4-hydroxycinnamic acid biphenyl ester, cinnamic acid 8-hydroxyoctyl ester, cinnamic acid 6-hydroxyhexyl ester, cinnamic acid 4-hydroxybutyl ester, cinnamic acid 3-hydroxypropyl ester, cinnamic acid 2-hydroxyethyl ester, cinnamic acid hydroxymethyl ester, 4-(8-hydroxyoctyloxy)azobenzene, 4-(6-hydroxyhexyloxy)azobenzene, 4-(4-hydroxybutyloxy)azobenzene, 4-(3-hydroxypropyloxy)azobenzene, 4-(2-hydroxyethyloxy)azobenzene, 4-hydroxymethyloxyazobenzene, 4-hydroxyazobenzene, 4-(8-hydroxyoctyloxy)chalcone, 4-(6-hydroxyhexyloxy)chalcone, 4-(4-hydroxybutyloxy)chalcone, 4-(3-hydroxypropyloxy)chalcone, 4-(2-hydroxyethyloxy)chalcone, 4-hydroxymethyloxychalcone, 4-hydroxychalcone, 4'-(8-hydroxyoctyloxy)chalcone, 4'-(6-hydroxyhexyloxy)chalcone, 4'-(4-hydroxybutyloxy)chalcone, 4'-(3-hydroxypropyloxy)chalcone, 4'-(2-hydroxyethyloxy)chalcone, 4'-hydroxymethyloxychalcone, 4'-hydroxychalcone, 7-(8-hydroxyoctyloxy)coumarin, 7-(6-hydroxyhexyloxy)coumarin, 7-(4-hydroxybutyloxy)coumarin, 7-(3-hydroxypropyloxy)coumarin, 7-(2-hydroxyethyloxy)coumarin, 7-hydroxymethyloxycoumarin, 7-hydroxycoumarin, 6-hydroxyoctyloxycoumarin, 6-hydroxyhexyloxycoumarin, 6-(4-hydroxybutyloxy)coumarin, 6-(3-hydroxypropyloxy)coumarin, 6-(2-hydroxyethyloxy)coumarin, 6-hydroxymethyloxycoumarin, and 6-hydroxycoumarin.

Specific examples of the compound that is the component (A) having a photo-aligning group and a carboxy group include cinnamic acid, ferulic acid, 4-nitrocinnamic acid, 4-methoxycinnamic acid, 3,4-dimethoxycinnamic acid, coumarin-3-carboxylic acid, and 4-(N,N-dimethylamino)cinnamic acid.

Specific examples of the compound that is the component (A) having a photo-aligning group and an amino group include 4-aminocinnamic acid methyl ester, 4-aminocinnamic acid ethyl ester, 3-aminocinnamic acid methyl ester, and 3-aminocinnamic acid ethyl ester.

Specific examples of a compound that is the component (D) and having a photo-aligning group and an alkoxysilyl group include
4-(3-trimethoxysilylpropyloxy)cinnamic acid methyl ester,
4-(3-triethoxysilylpropyloxy)cinnamic acid methyl ester,
4-(3-trimethoxysilylpropyloxy)cinnamic acid ethyl ester,
4-(3-triethoxysilylpropyloxy)cinnamic acid ethyl ester,
4-(6-trimethoxysilylhexyloxy)cinnamic acid methyl ester,
4-(6-triethoxysilylhexyloxy)cinnamic acid methyl ester,
4-(6-trimethoxysilylhexyloxy)cinnamic acid ethyl ester, and
4-(6-triethoxysilylhexyloxy)cinnamic acid ethyl ester.

Examples of the low-molecular alignment component that is the component (A) include the specific examples above, but are not limited to these.

When the low-molecular alignment component that is the component (A) is the compound having a photo-aligning group and a hydroxy group, as the component (A), a compound having in the molecule two or more photo-aligning groups and/or two or more hydroxy groups can be used. More specifically, as the component (A), a compound having in the molecule one hydroxy group and two or more photo-aligning groups, a compound having in the molecule one photo-aligning group and two or more hydroxy groups, or a compound having in the molecule two or more photo-aligning groups and two or more hydroxy groups can be used. Examples of the compound having in the molecule two or more photo-aligning groups and two or more hydroxy groups include a compound of the following Formula:

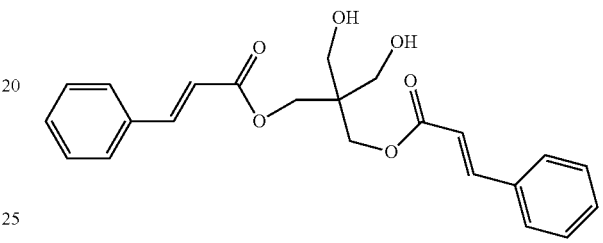

By suitably selecting these compounds, the molecular weight of the low-molecular alignment component that is the component (A) can be controlled within a desired range. To form a cured film of the present embodiment using the composition of the present invention, thermal curing is necessary. When heating for the curing is performed, the low-molecular alignment component that is the component (A) can be prevented from sublimating.

The compound of the component (A) in the composition of the present invention may be a mixture of a plurality of compounds having a photo-aligning group and any one of a hydroxy group, a carboxy group, an amino group, and an alkoxysilyl group.

The composition of the present invention contains, as the component (A), a compound having the photo-aligning group of Formula [1]:

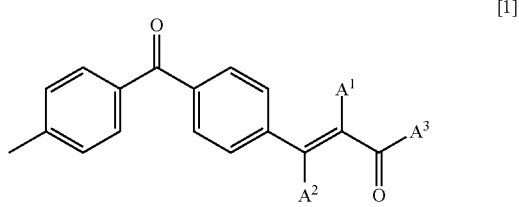

(In Formula [1], $A^1$ and $A^2$ are independently a hydrogen atom or a methyl group;

$A^3$ is a hydroxy group, a mercapto group, an amino group, a $C_{1-10}$ alkoxy group, a $C_{1-10}$ alkylthio group, a $C_{1-10}$ alkylamino group, a phenoxy group, a phenylthio group, a phenyl amino group, a biphenyl amino group, a phenyl group, or a biphenyl group, in which hydrogen atoms on the phenylene group and on the phenyl group are independently and optionally substituted with at least one substituent selected from a $C_{1-10}$ alkyl group, a $C_{1-10}$ alkoxy group, a halogen atom, a cyano group, and a nitro group.)

The hydrogen atom or the methyl group is preferred as $A^1$, the hydrogen atom is preferred as $A^2$, and the $C_{1-10}$ alkoxy group, the phenyl group, or the like is preferred as $A^3$.

Specific examples of a compound having the photo-aligning group of Formula [1] and a hydroxy group include 4-[4-(8-hydroxyoctyloxy)benzoyl]cinnamic acid methyl ester, 4-[4-(6-hydroxyhexyloxy)benzoyl]cinnamic acid methyl ester, 4-[4-(4-hydroxybutyloxy)benzoyl]cinnamic acid methyl ester, 4-[4-(3-hydroxypropyloxy)benzoyl]cinnamic acid methyl ester, 4-[4-(2-hydroxyethyloxy)benzoyl]cinnamic acid methyl ester, 4-[4-hydroxymethyloxy benzoyl]cinnamic acid methyl ester, 4-[4-hydroxy benzoyl]cinnamic acid methyl ester, 4-[4-(8-hydroxyoctyloxy)benzoyl]cinnamic acid ethyl ester, 4-[4-(6-hydroxyhexyloxy)benzoyl]cinnamic acid ethyl ester, 4-[4-(4-hydroxybutyloxy)benzoyl]cinnamic acid ethyl ester, 4-[4-(3-hydroxypropyloxy)benzoyl]cinnamic acid ethyl ester, 4-[4-(2-hydroxyethyloxy)benzoyl]cinnamic acid ethyl ester, 4-[4-hydroxymethyloxy benzoyl]cinnamic acid ethyl ester, 4-[4-hydroxy benzoyl]cinnamic acid ethyl ester, 4-[4-(8-hydroxyoctyloxy)benzoyl]cinnamic acid tertiary butyl ester, 4-[4-(6-hydroxyhexyloxy)benzoyl]cinnamic acid tertiary butyl ester, 4-[4-(4-hydroxybutyloxy)benzoyl]cinnamic acid tertiary butyl ester, 4-[4-(3-hydroxypropyloxy)benzoyl]cinnamic acid tertiary butyl ester, 4-[4-(2-hydroxyethyloxy)benzoyl]cinnamic acid tertiary butyl ester, 4-[4-hydroxymethyloxy benzoyl]cinnamic acid tertiary butyl ester, 4-[4-(8-hydroxyoctyloxy)benzoyl]cinnamic acid phenyl ester, 4-[4-(6-hydroxyhexyloxy)benzoyl]cinnamic acid phenyl ester, 4-[4-(4-hydroxybutyloxy)benzoyl]cinnamic acid phenyl ester, 4-[4-(3-hydroxypropyloxy)benzoyl]cinnamic acid phenyl ester, 4-[4-(2-hydroxyethyloxy)benzoyl]cinnamic acid phenyl ester, 4-[4-hydroxymethyloxy benzoyl]cinnamic acid phenyl ester, 4-[4-hydroxy benzoyl]cinnamic acid phenyl ester, 4-[4-(8-hydroxyoctyloxy)benzoyl]cinnamic acid biphenyl ester, 4-[4-(6-hydroxyhexyloxy)benzoyl]cinnamic acid biphenyl ester, 4-[4-(4-hydroxybutyloxy)benzoyl]cinnamic acid biphenyl ester, 4-[4-(3-hydroxypropyloxy)benzoyl]cinnamic acid biphenyl ester, 4-[4-(2-hydroxyethyloxy)benzoyl]cinnamic acid biphenyl ester, 4-[4-hydroxymethyloxy benzoyl]cinnamic acid biphenyl ester, 4-[4-hydroxy benzoyl]cinnamic acid biphenyl ester, 4-benzoyl cinnamic acid 8-hydroxyoctyl ester, 4-benzoyl cinnamic acid 6-hydroxyhexyl ester, 4-benzoyl cinnamic acid 4-hydroxybutyl ester, 4-benzoyl cinnamic acid 3-hydroxypropyl ester, 4-benzoyl cinnamic acid 2-hydroxyethyl ester, 4-benzoyl cinnamic acid hydroxymethyl ester, 4-[4-(8-hydroxyoctyloxy)benzoyl]chalcone, 4-[4-(6-hydroxyhexyloxy)benzoyl]chalcone, 4-[4-(4-hydroxybutyloxy)benzoyl]chalcone, 4-[4-(3-hydroxypropyloxy)benzoyl]chalcone, 4-[4-(2-hydroxyethyloxy)benzoyl]chalcone, 4-(4-hydroxymethyloxy benzoyl)chalcone, 4-(4-hydroxybenzoyl)chalcone, 4-[4-(8-hydroxyoctyloxy)benzoyl]chalcone, 4'-[4-(6-hydroxyhexyloxy)benzoyl]chalcone, 4'-[4-(4-hydroxybutyloxy)benzoyl]chalcone, 4-[4-(3-hydroxypropyloxy)benzoyl]chalcone, 4-[4-(2-hydroxyethyloxy)benzoyl]chalcone, 4'-(4-hydroxymethyloxy benzoyl)chalcone, and 4'-(4-hydroxybenzoyl)chalcone.

Specific examples of a compound having the photo-aligning group of Formula [1] and a carboxy group include 4-benzoyl cinnamic acid, 4-(4-nitrobenzoyl)cinnamic acid, 4-(4-methoxybenzoyl)cinnamic acid, and 4-(3,4-dimethoxybenzoyl)cinnamic acid.

Specific examples of a compound having the photo-aligning group of Formula [1] and an amino group include 4-(4-aminobenzoyl)cinnamic acid methyl ester, 4-(4-aminobenzoyl)cinnamic acid ethyl ester, 4-(4-aminobenzoyl)cinnamic acid tertiary butyl ester, 4-(3-aminobenzoyl)cinnamic acid methyl ester, 4-(3-aminobenzoyl)cinnamic acid ethyl ester, and 4-(3-aminobenzoyl)cinnamic acid tertiary butyl ester.

Specific examples of a compound having the photo-aligning group of Formula [1] and an alkoxysilyl group include 4-[4-(3-trimethoxysilylpropyloxy)benzoyl]cinnamic acid methyl ester, 4-[4-(3-triethoxysilylpropyloxy)benzoyl]cinnamic acid methyl ester, 4-[4-(3-trimethoxysilylpropyloxy)benzoyl]cinnamic acid ethyl ester, 4-[4-(3-triethoxysilylpropyloxy)benzoyl]cinnamic acid ethyl ester, 4-[4-(3-trimethoxysilylpropyloxy)benzoyl]cinnamic acid tertiary butyl ester, 4-[4-(3-triethoxysilylpropyloxy)benzoyl]cinnamic acid tertiary butyl ester, 4-[4-(6-trimethoxysilylhexyloxy)benzoyl]cinnamic acid methyl ester, 4-[4-(6-triethoxysilylhexyloxy)benzoyl]cinnamic acid methyl ester, 4-[4-(6-trimethoxysilylhexyloxy)benzoyl]cinnamic acid ethyl ester, 4-[4-(6-triethoxysilylhexyloxy)benzoyl]cinnamic acid ethyl ester, 4-[4-(6-trimethoxysilylhexyloxy)benzoyl]cinnamic acid tertiary butyl ester, and 4-[4-(6-triethoxysilylhexyloxy)benzoyl]cinnamic acid tertiary butyl ester.

Examples of a compound having the group of Formula [1] as the photo-aligning group include a compound of Formula [2]:

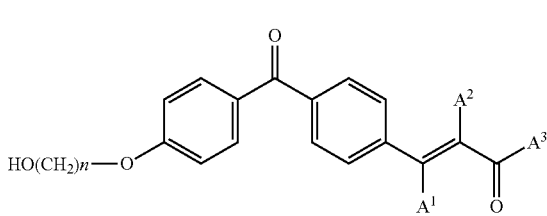

[2]

(In Formula [2], $A^1$ and $A^2$ are independently a hydrogen atom or a methyl group;

$A^3$ is a hydroxy group, a mercapto group, an amino group, a $C_{1-10}$ alkoxy group, a $C_{1-10}$ alkylthio group, a $C_{1-10}$ alkylamino group, a phenoxy group, a phenylthio group, a phenyl amino group, a biphenyl amino group, a phenyl group, or a biphenyl group, in which hydrogen atoms on the phenylene group and on the phenyl group are independently and optionally substituted with at least one substituent selected from a $C_{1-10}$ alkyl group, a $C_{1-10}$ alkoxy group, a halogen atom, a cyano group, and a nitro group; and n is an integer of 2 to 20.)

This compound is a new compound that has not been described in the literature, and can be produced, for example, by a method illustrated in the following scheme:

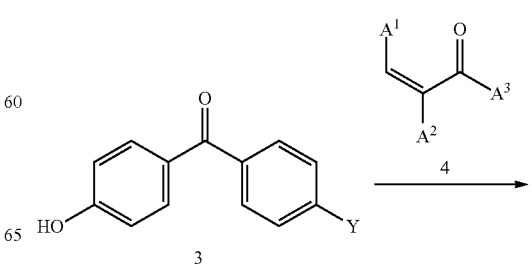

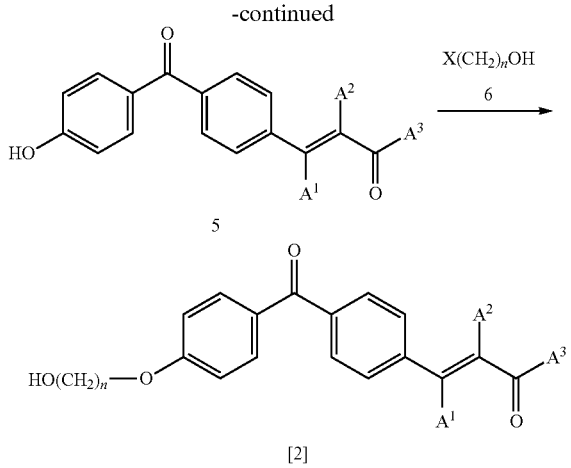

[2]

The compound of Formula 5 can be synthesized by subjecting the benzophenone compound of Formula 3 and a compound of Formula 4 selected from (meth)acrylic acid ester, (meth)acrylic acid thioester, vinyl ketone, and the like to coupling reaction such as the Heck reaction in the coexistence of a metal complex catalyst, a ligand, and a base.

In the compound of Formula 3, Y is a substituent that can be desorbed, and examples of the substituent used include halogen atoms of F, Cl, Br, and I, for example; and sulfonic acid ester groups such as a p-toluenesulfonic acid ester group ($-OSO_2C_6H_4$-p-$CH_3$), a methanesulfonic acid ester group ($-OSO_2CH_3$), a trifluoromethanesulfonic acid ester group ($-OSO_2CF_3$). Among them, Br, I, and the trifluoromethanesulfonic acid ester group are preferred from the viewpoint of reactivity.

The amount used of the compound of Formula 4 is preferably, but is not limited to, 1.0 molar equivalent to 3.0 molar equivalents to the compound of Formula 3. The amount is more preferably 1.0 molar equivalent to 1.2 molar equivalents.

In this reaction, a suitable metal complex and a ligand are used to form a metal complex catalyst to be used. In general, as the metal complex, a palladium complex or a nickel complex is used, and a copper catalyst is preferably used to coexist as a promoter depending on the reaction.

As the metal complex catalyst, while those in various structures may be used, a palladium complex or a nickel complex of what is called a low-valent metal is preferably used, and particularly zero-valent metal complex catalysts having tertiary phosphine or tertiary phosphite as a ligand are preferred. Alternatively, a suitable precursor may be used that is easily transformed into a zero-valent metal complex catalyst in the reaction system. Furthermore, in the reaction system, a metal complex that does not contain tertiary phosphine or tertiary phosphite as a ligand and tertiary phosphine or tertiary phosphite that is a ligand to form a low-valent metal complex catalyst containing tertiary phosphine or tertiary phosphite as a ligand.

Examples of the tertiary phosphine and the tertiary phosphite being ligands include triphenylphosphine, tri-o-tolylphosphine, diphenylmethylphosphine, phenyldimethylphosphine, 1,2-bis(diphenylphosphino)ethane, 1,3-bis(diphenylphosphino)propane, 1,4-bis(diphenylphosphino)butane, 1,1'-bis(diphenylphosphino)ferrocene, trimethyl phosphite, triethyl phosphite, and triphenyl phosphite. A metal complex catalyst that contains a mixture of two or more of these ligands is also preferably used.

As the metal complex catalyst, a palladium complex that does not contain tertiary phosphine or tertiary phosphite and a metal complex that contains tertiary phosphine or tertiary phosphite are also preferably used in combination. In this case, the ligands described above may be further combined therewith. Examples of the palladium complex that does not contain tertiary phosphine or tertiary phosphite include bis(benzylideneacetone)palladium, tris(benzylideneacetone)dipalladium, bis(acetonitrile)dichloropalladium, bis(benzonitrile)dichloropalladium, palladium acetate, palladium chloride, and palladium-activated carbon. Examples of a palladium complex that contains tertiary phosphine or tertiary phosphite as a ligand include (ethylene)bis(triphenyl phosphine)palladium, tetrakis(triphenyl phosphine)palladium, and bis(triphenyl phosphine)dichloropalladium.

As the metal complex catalyst, the palladium complex that does not contain tertiary phosphine or tertiary phosphite may be used alone.

The amount of these palladium complexes used may be what is called catalytic amount, and is preferably 20% by mole or less, and particularly preferably 10% by mole or less with respect to the compound of Formula 3. The copper catalyst used as a promoter at the same time is preferably monovalent, and examples thereof include copper chloride (I), copper bromide (I), copper iodide (I), and copper acetate (I).

Examples of the base that can be used include inorganic bases such as sodium hydroxide, potassium hydroxide, lithium hydroxide, sodium hydrogen carbonate, potassium hydrogen carbonate, sodium phosphate, potassium phosphate, sodium carbonate, potassium carbonate, lithium carbonate, and cesium carbonate; amine such as methylamine, dimethylamine, trimethylamine, ethylamine, diethylamine, triethylamine, propylamine, dipropylamine, tripropylamine, isopropylamine, diisopropylamine, triisopropylamine, butylamine, dibutylamine, tributylamine, diisopropylethylamine, pyridine, imidazole, quinoline, collidine, pyrrolidine, piperidine, morpholine, and N-methylmorpholine; and sodium acetate, potassium acetate, and lithium acetate. These bases can be suitably selected in consideration of easy occurrence of the reaction, and in this case, the bases may be used singly or in combination of two or more of them.

The amount of the bases used is preferably 20% by mole or less, and particularly preferably 10% by mole or less with respect to the compound of Formula 3.

Any reaction solvent may be used as long as it is stable and inert and does not prevent the reaction under this reaction condition. Examples of the reaction solvent that can be used include water, alcohols (e.g., methanol, ethanol, propanol, isopropanol, butanol, octanol, etc.), amines (pyridine, triethylamine, etc.), aprotic polar organic solvent (dimethylformamide (DMF), dimethylsulfoxide (DMSO), dimethylacetamide (DMAc), N-methylpyrrolidone (NMP), etc.), ethers ($Et_2O$, i-$Pr_2O$, TBME, CPME, THF, dioxane, etc.), aliphatic hydrocarbons (pentane, hexane, heptane, petroleum ether, etc.), aromatic hydrocarbons (benzene, toluene, xylene, mesitylene, chlorobenzene, dichlorobenzene, nitrobenzene, tetralin, etc.), halogenated hydrocarbons (chloroform, dichloromethane, carbon tetrachloride, dichloroethane, etc.), lower fatty acid esters (methyl acetate, ethyl acetate, butyl acetate, methyl propionate, etc.), and nitriles (acetonitrile, propionitrile, butyronitrile, etc.). These solvents can be suitably selected in consideration of easy occurrence of the reaction, and may be used singly or in combination of two or more of them. In some cases, these solvents may be used as solvents that do not contain water by using a suitable dehydrating agent or a desiccating agent.

Although the amount used (the reaction concentration) of the solvent is not limited to a particular value, the reaction may be performed without the solvent, or the solvent may be used in an amount 0.1 to 100 times by mass the amount of the compound of Formula 3. The amount used is preferably 1 to 10 times by mass, and more preferably 2 to 5 times by mass.

Although the reaction temperature may be preferably selected from a temperature range from −100° C. to the boiling point of the reaction solvent, the reaction temperature is more preferably −50° C. to 200° C., and particularly preferably 20° C. to 150° C. The reaction time is 0.1 to 1000 hours, and more preferably 0.5 to 100 hours.

The compound of Formula 5 obtained by the method indicated in the reaction formulae described above is preferably purified by distillation, recrystallization, or column chromatography using silica gel or the like. The recrystallization is preferably performed at a temperature as low as possible.

The compound of Formula [2] can be synthesized by performing the Williamson ether synthesis in the coexistence of the bases of Formula 5 and Formula 6.

In the compound of Formula 6, X is a substituent that can be desorbed, and examples of the substituent used include halogen atoms of F, Cl, Br, and I; and sulfonic acid ester groups such as p-toluenesulfonic acid ester group (—OSO$_2$C$_6$H$_4$-p-CH$_3$), methanesulfonic acid ester group (—OSO$_2$CH$_3$), and trifluoromethanesulfonic acid ester group (—OSO$_2$CF$_3$). Among them, Cl, Br, I, and the trifluoromethanesulfonic acid ester group are preferred from the viewpoint of reactivity and costs.

The amount used of the compound of Formula 6 is preferably, but is not limited to, 1.0 molar equivalent to 3.0 molar equivalents to the compound of Formula 5. The amount is more preferably 1.0 molar equivalent to 1.2 molar equivalents.

In this reaction, a suitable base is used. Examples of the base that can be generally used include inorganic bases such as sodium hydroxide, potassium hydroxide, lithium hydroxide, sodium hydrogen carbonate, potassium hydrogen carbonate, sodium phosphate, potassium phosphate, sodium carbonate, potassium carbonate, lithium carbonate, and cesium carbonate; bases such as sodium tert-butoxide, potassium tert-butoxide, sodium hydride, and potassium hydride; and amines such as trimethylamine, triethylamine, tripropylamine, triisopropylamine, tributylamine, diisopropylethylamine, pyridine, imidazole, quinoline, and collidine. These bases can be suitably selected in consideration of easy occurrence of the reaction, and in this case, the bases may be used singly or in combination of two or more of them.

The amount of the bases used is preferably 1.0 equivalent to 3.0 equivalents to the compound of Formula 5. The amount is more preferably 1.0 equivalent to 1.5 equivalents.

Any reaction solvent may be used as long as it is stable and inert and does not prevent the reaction under this reaction condition. Examples of the reaction solvent that can be used include aprotic polar organic solvents (DMF, DMSO, DMAc, NMP, etc.), ethers (Et$_2$O, i-Pr$_2$O, TBME, CPME, THF, dioxane, etc.), aliphatic hydrocarbons (pentane, hexane, heptane, petroleum ether, etc.), aromatic hydrocarbons (benzene, toluene, xylene, mesitylene, chlorobenzene, dichlorobenzene, nitrobenzene, tetralin, etc.), halogenated hydrocarbons (chloroform, dichloromethane, carbon tetrachloride, dichloroethane, etc.), lower fatty acid esters (methyl acetate, ethyl acetate, butyl acetate, methyl propionate, etc.), and nitriles (acetonitrile, propionitrile, butyronitrile, etc.). These solvents can be suitably selected in consideration of easy occurrence of the reaction, and in this case, the solvents may be use singly or in combination of two or more of them. In some cases, these solvents may be used as nonaqueous solvents by using a suitable dehydrating agent or a desiccating agent.

Although the amount used (the reaction concentration) of the solvent is not limited to a particular value, the reaction may be performed without the solvent, or the solvent may be used in an amount 0.1 to 100 times by mass the amount of the compound of Formula 5. The amount used is preferably 1 to 10 times by mass, and more preferably 2 to 5 times by mass.

To cause the reaction to effectively proceed, tetra-n-butylammonium iodide, sodium iodide, potassium iodide, or the like may be added.

Although the reaction temperature may be preferably selected from a temperature range from −100° C. to the boiling point of the reaction solvent, the reaction temperature is more preferably −50° C. to 200° C., and particularly preferably 20° C. to 150° C. The reaction time is 0.1 to 1000 hours, and more preferably 0.5 to 100 hours.

The compound of Formula 5 obtained by the method indicated in the reaction formulae described above is preferably purified by distillation, recrystallization, or column chromatography using silica gel or the like. The recrystallization is preferably performed at a temperature as low as possible.

As a method for producing the compound of Formula [2], other than the scheme described above, a method may be used in which the compound can be produced by performing the Williamson ether synthesis using Formula 3 and Formula 6, and then performing coupling reaction such as the Heck reaction with Formula 4 in the coexistence of a metal complex catalyst, a ligand, and a base.

[Component (B)]

The component (B) of the composition of the present invention is at least one polymer selected from a component (B-1): a polymer that has at least one substituent selected from the group consisting of a hydroxy group, a carboxy group, an amino group, and an alkoxysilyl group, a component (B-2): a polymer that has a substituent capable of thermally reacting with the component (A) and is self-crosslinkable, and a component (B-3): a melamine formaldehyde resin. The following describes each of the components in detail.

[Component (B-1)]

The component (B-1) is a polymer (hereinafter, also called "specific (co)polymer 1") having at least one substituent selected from the group consisting of a hydroxy group, a carboxy group, an amino group, and an alkoxysilyl group.

Examples of the polymer that is the component (B-1) include a polymer having a straight-chain structure or a branched structure such as an acrylic polymer, polyamic acid, polyimide, polyvinyl alcohol, polyester, polyester polycarboxylic acid, polyether polyol, polyester polyol, polycarbonate polyol, polycaprolactone polyol, polyalkylene imine, polyallylamine, celluloses(cellulose or derivatives thereof), and a phenol novolac resin; and a cyclic polymer such as cyclodextrins.

Among them, as the acrylic polymer, a polymer obtained by polymerizing a monomer having an unsaturated double bond such as an acrylic acid ester, a methacrylic acid ester, and styrene can be used.

As a method for synthesizing the acrylic polymer being an example of the component (B-1), a method for (co)polymerizing a monomer having at least one substituent selected from the group consisting of a hydroxy group, a carboxy group, an amino group, and an alkoxysilyl group with a monomer other than the monomer if desired is simple.

Examples of the monomer having at least one substituent selected from the group consisting of a hydroxy group, a carboxy group, an amino group, and an alkoxysilyl group include a monomer having a hydroxy group such as 2-hydroxyethyl acrylate, 2-hydroxyethyl methacrylate, 2-hydroxypropyl acrylate, 2-hydroxypropyl methacrylate, 4-hydroxybutyl acrylate, 4-hydroxybutyl methacrylate, 2,3-dihydroxypropyl acrylate, 2,3-dihydroxypropyl methacrylate, diethylene glycol monoacrylate, diethylene glycol monomethacrylate, caprolactone 2-(acryloyloxy) ethyl ester, caprolactone 2-(methacryloyloxy)ethyl ester, poly(ethylene glycol)ethylether acrylate, poly(ethylene glycol)ethylether methacrylate, 5-acryloyloxy-6-hydroxynorbornene-2-carboxylic-6-lactone, and 5-methacryloyloxy-6-hydroxynorbornene-2-carboxylic-6-lactone; a monomer having a carboxy group such as acrylic acid, methacrylic acid, crotonic acid, mono-(2-(acryloyloxy)ethyl)phthalate, mono-(2-(methacryloyloxy)ethyl)phthalate, vinylbenzoic acid, N-(carboxyphenyl)maleimide, N-(carboxyphenyl) methacrylamide, and N-(carboxyphenyl)acrylamide; a monomer having a phenolic hydroxy group such as p-hydroxystyrene, m-hydroxystyrene, o-hydroxystyrene, N-(hydroxyphenyl)methacrylamide, N-(hydroxyphenyl)acrylamide, N-(hydroxyphenyl)maleimide, and N-(hydroxyphenyl) maleimide; a monomer having an amino group such as aminoethyl acrylate, aminoethyl methacrylate, aminopropyl acrylate, and aminopropyl methacrylate; and a monomer having a triethyl alkoxysilyl group such as trimethoxysilyl propyl acrylate, trimethoxysilylpropyl methacrylate, triethoxysilyl propylacrylate, and triethoxysilylpropyl methacrylate.

In the present invention, when the acrylic polymer being an example of the component (B-1) is obtained, in addition to the monomer having at least one substituent selected from the group consisting of a hydroxy group, a carboxy group, an amino group, and an alkoxysilyl group, another monomer can be used that can be copolymerized with the monomer and does not have a substituent selected from the group consisting of a hydroxy group, a carboxy group, an amino group, and an alkoxysilyl group.

Specific examples of such a monomer include an acrylic acid ester compound, a methacrylic acid ester compound, a maleimide compound, an acrylamide compound, acrylonitrile, maleic anhydride, a styrene compound, and a vinyl compound.

Specific examples of the monomer are described below, but the monomer is not limited to these.

Examples of the acrylic acid ester compound include methyl acrylate, ethyl acrylate, propyl acrylate, isopropyl acrylate, butyl acrylate, isobutyl acrylate, t-butyl acrylate, benzyl acrylate, naphthyl acrylate, anthryl acrylate, anthrylmethyl acrylate, phenyl acrylate, glycidyl acrylate, 2,2,2-trifluoroethyl acrylate, cyclohexyl acrylate, isobornyl acrylate, 2-methoxyethyl acrylate, methoxytriethylene glycol acrylate, 2-ethoxyethyl acrylate, 2-aminoethyl acrylate, tetrahydrofurfuryl acrylate, 3-methoxybutyl acrylate, 2-methyl-2-adamanthyl acrylate, 2-propyl-2-adamanthyl acrylate, 8-methyl-8-tricyclodecyl acrylate, and 8-ethyl-8-tricyclodecyl acrylate.

Examples of the methacrylic acid ester compound include methyl methacrylate, ethyl methacrylate, propyl methacrylate, isopropyl methacrylate, butyl methacrylate, isobutyl methacrylate, t-butyl methacrylate, benzyl methacrylate, naphthyl methacrylate, anthryl methacrylate, anthrylmethyl methacrylate, phenyl methacrylate, glycidyl methacrylate, 2,2,2-trifluoroethyl methacrylate, cyclohexyl methacrylate, isobornyl methacrylate, 2-methoxyethyl methacrylate, methoxy triethylene glycol methacrylate, 2-ethoxy ethyl methacrylate, 2-aminomethyl methacrylate, tetrahydrofurfuryl methacrylate, 3-methoxybutyl methacrylate, 2-methyl-2-adamanthyl methacrylate, γ-butyrolactone methacrylate, 2-propyl-2-adamanthyl methacrylate, 8-methyl-8-tricyclodecyl methacrylate, and 8-ethyl-8-tricyclodecyl methacrylate.

Examples of the vinyl compound include methylvinyl ether, benzylvinyl ether, vinyl naphthalene, vinyl carbazole, allyl glycidyl ether, 3-ethenyl-7-oxabicyclo[4.1.0]heptane, 1,2-epoxy-5-hexene, and 1,7-octadiene mono epoxide.

Examples of the styrene compound include styrene, methylstyrene, chlorostyrene, and bromostyrene.

Examples of the maleimide compound include maleimide, N-methylmaleimide, N-phenylmaleimide, and N-cyclohexyl maleimide.

The amount used of the monomer, having at least one substituent selected from the group consisting of a hydroxy group, a carboxy group, an amino group, and an alkoxysilyl group, used to obtain the acrylic polymer being an example of the component (B-1) is preferably 5% by mole to 100% by mole based on the total amount of all monomers used to obtain the acrylic polymer being an example of the component (B-1).

Although the method for obtaining the acrylic polymer being an example of the component (B-1) is not limited to a particular method, the acrylic polymer can be obtained, for example, by subjecting the monomer having at least one substituent selected from the group consisting of a hydroxy group, a carboxy group, an amino group, and an alkoxysilyl group, the monomer that does not have a substituent selected from the group consisting of a hydroxy group, a carboxy group, an amino group, and an alkoxysilyl group if desired, and a polymerization initiator or the like to polymerization reaction in a solvent in which they coexist at a temperature of 50° C. to 110° C. The solvent used herein is not limited as long as the solvent can dissolve the monomer having at least one substituent selected from the group consisting of a hydroxy group, a carboxy group, an amino group, and an alkoxysilyl group, the monomer that does not have a substituent selected from the group consisting of a hydroxy group, a carboxy group, an amino group, and an alkoxysilyl group if desired, and a polymerization initiator or the like. Specific examples thereof will be described in [Solvent] described below.

The acrylic polymer being an example of the component (B-1) obtained by the method described above is generally in a state of a solution being dissolved in the solvent.

A solution of the acrylic polymer being an example of the component (B-1) obtained by the method described above is poured into diethyl ether, water, or the like with stirring and the acrylic polymer is reprecipitated. The precipitate thus obtained is filtered and washed, and then is dried at room temperature or dried by heating under atmospheric pressure or reduced pressure. Thus, a powder of the acrylic polymer being an example of the component (B-1) can be prepared. By this operation, the polymerization initiator and an unreacted monomer that coexist with the acrylic polymer being an example of the component (B-1) can be removed, and consequently, a powder of the purified acrylic polymer as an example of the component (B-1) can be obtained. If the acrylic polymer cannot be sufficiently purified by one operation, the obtained powder may be redissolved in a solvent, followed by repeating the operation described above.

The acrylic polymer being an example of the component (B-1) has a weight-average molecular weight of preferably 3,000 to 200,000, more preferably 4,000 to 150,000, and still more preferably 5,000 to 100,000. An excessively high weight-average molecular weight exceeding 200,000 may reduce the solubility in solvent, so that the handling property may deteriorate, and an excessively low weight-average molecular weight below 3,000 may cause insufficient curing during heat curing, so that the solvent resistance and the heat resistance may decrease. The weight-average molecular weight herein is a value obtained by gel permeation chromatography (GPC) using polystyrene as the standard sample. The same method is used hereinafter in the present specification.

Examples of the polyether polyol being one preferred example of the specific (co)polymer 1 of the component (B-1) include those obtained by adding propylene oxide, polyethylene glycol, or polypropylene glycol, or the like, to polyhydric alcohol such as polyethylene glycol, polypropylene glycol, propylene glycol, bisphenol A, triethylene glycol, and sorbitol. Specific examples of the polyether polyol include ADEKA polyether P-series, G-series, EDP-series, BPX-series, FC-series, and CM-series manufactured by ADEKA Corporation; and UNIOX (registered trademark) HC-40, HC-60, ST-30E, ST-40E, G-450, and G-750, UNIOL (registered trademark) TG-330, TG-1000, TG-3000, TG-4000, HS-1600D, DA-400, DA-700, and DB-400, and NONION (registered trademark) LT-221, ST-221, and OT-221 manufactured by NOF Corporation.

Examples of the polyester polyol being one preferred example of the specific (co)polymer of the component (B-1) include those obtained by causing polyhydric carboxylic acid such as adipic acid, sebacic acid, and isophthalic acid to react with diol such as ethylene glycol, propylene glycol, butylene glycol, polyethylene glycol, and polypropylene glycol. Specific examples of the polyester polyol include POLYLITE (registered trademark) OD-X-286, OD-X-102, OD-X-355, OD-X-2330, OD-X-240, OD-X-668, OD-X-2108, OD-X-2376, OD-X-2044, OD-X-688, OD-X-2068, OD-X-2547, OD-X-2420, OD-X-2523, OD-X-2555, OD-X-2560 manufactured by DIC corporation; and Polyol P-510, P-1010, P-2010, P-3010, P-4010, P-5010, P-6010, F-510, F-1010, F-2010, F-3010, P-1011, P-2011, P-2013, P-2030, N-2010, and PNNA-2016 manufactured by Kuraray Co., Ltd.

Examples of the polycaprolactone polyol being one preferred example of the specific (co)polymer of the component (B-1) include those obtained by performing ring-opening polymerization of c-caprolactone using polyhydric alcohol such as trimethylolpropane and ethylene glycol as an initiator. Specific examples of the polycaprolactone polyol include POLYLITE (registered trademark) OD-X-2155, OD-X-640, and OD-X-2568 manufactured by DIC Corporation; and PLACCEL (registered trademark) 205, L205AL, 205U, 208, 210, 212, L212AL, 220, 230, 240, 303, 305, 308, 312, and 320 manufactured by Daicel Chemical Industries, Ltd.

Examples of the polycarbonate polyol being one preferred example of the specific (co)polymer of the component (B-1) include those obtained by causing polyhydric alcohol such as trimethylolpropane and ethylene glycol to react with diethyl carbonate, diphenyl carbonate, ethylene carbonate, or the like. Specific examples of the polycarbonate polyol include PLACCEL (registered trademark) CD205, CD205PL, CD210, and CD220 manufactured by Daicel Chemical Industries, Ltd and C-590, C-1050, C-2050, C-2090, and C-3090 manufactured by Kuraray Co., Ltd.

Examples of the cellulose being one preferred example of the specific (co)polymer 1 of the component (B-1) include hydroxyalkyl celluloses such as hydroxyethyl cellulose and hydroxypropyl cellulose; hydroxyalkyl alkyl celluloses such as hydroxyethyl methyl cellulose, hydroxypropyl methyl cellulose, and hydroxyethyl ethyl cellulose; and cellulose. For example, the hydroxyalkyl celluloses such as hydroxyethyl cellulose and hydroxypropyl cellulose are preferred.

Examples of the cyclodextrin being one preferred example of the specific (co)polymer 1 of the component (B-1) include cyclodextrin such as α-cyclodextrin, β-cyclodextrin, and γ-cyclodextrin; methylated cyclodextrin such as methyl-α-cyclodextrin, methyl-β-cyclodextrin, and methyl-γ-cyclodextrin; and hydroxyalkyl cyclodextrin such as hydroxymethyl-α-cyclodextrin, hydroxymethyl-β-cyclodextrin, hydroxymethyl-γ-cyclodextrin, 2-hydroxyethyl-α-cyclodextrin, 2-hydroxyethyl-β-cyclodextrin, 2-hydroxyethyl-γ-cyclodextrin, 2-hydroxypropyl-α-cyclodextrin, 2-hydroxypropyl-β-cyclodextrin, 2-hydroxypropyl-γ-cyclodextrin, 3-hydroxypropyl-α-cyclodextrin, 3-hydroxypropyl-β-cyclodextrin, 3-hydroxypropyl-γ-cyclodextrin, 2,3-dihydroxypropyl-α-cyclodextrin, 2,3-dihydroxypropyl-β-cyclodextrin, and 2,3-dihydroxypropyl-γ-cyclodextrin.

Examples of the phenol novolac resin being one preferred example of the specific (co)polymer 1 of the component (B-1) include phenol-formaldehyde polycondensate.

In the composition of the present invention, the polymer of the component (B-1) may be used in a form of powder or in a form of solution in which the purified powder is redissolved in a solvent described below.

In the composition of the present invention, the component (B-1) may be a mixture of a plurality of polymers exemplified as the component (B-1).

[Component (B-2)]

In the cured-film formation composition of the present embodiment, the component (B-2) may be a polymer (hereinafter, also called "specific (co)polymer 2") that has a substituent capable of thermally reacting with the component (A) and is self-cross-linkable.

More specifically, the specific (co)polymer 2 is a polymer having a cross-linking substituent (hereinafter, the cross-linking substituent, the hydroxy group, the carboxy group, the amino group, and the alkoxysilyl group as a whole are also called "specific functional group") that causes thermal reaction with the component (A) and self-cross-linking reaction and reacts at a temperature lower than the sublimation temperature of the component (A). The thermal reaction between the component (A) and the component (B-2) can prevent the component (A) from sublimating. Thus, the cured-film formation composition of the present embodiment can form an orientation material having high photoreaction efficiency as a cured film as described above.

Examples of a preferred cross-linking substituent that the polymer of the component (B-2) contains include an alkoxymethylamide group and an alkoxysilyl group. The content of such a cross-linking substituent is preferably 0.5 to 1 per repeating unit of the component (B-2), and more preferably 0.8 to 1 from the viewpoint of solvent resistance of the orientation material.

As the polymer of the component (B-2), it is possible to use, for example, a polymer produced by using an acrylamide compound or a methacrylamide compound that is substituted with a hydroxymethyl group or an alkoxymethyl group such as N-hydroxymethylacrylamide, N-methoxymethylmethacrylamide, N-ethoxymethyl acrylamide, and N-butoxymethyl methacrylamide.

Examples of this polymer include poly(N-butoxymethyl acrylamide), a copolymer of N-butoxymethyl acrylamide with styrene, a copolymer of N-hydroxymethyl methacrylamide with methyl methacrylate, a copolymer of N-ethoxymethyl methacrylamide with benzyl methacrylate, and a copolymer of N-butoxymethyl acrylamide with benzyl methacrylate and 2-hydroxypropyl methacrylate.

As the component (B-2), a polymer produced by using a compound having an alkoxysilyl group can also be used.

Examples of this polymer include poly(3-methacryloxypropyl trimethoxy silane), a copolymer of 3-methacryloxypropyl trimethoxy silane with styrene, poly(3-acryloxypropyl trimethoxy silane), and a copolymer of 3-acryloxypropyl trimethoxy silane with methyl methacrylate.

In addition to the specific (co)polymer 2 used for the cured-film formation composition of the present embodiment, a monomer (hereinafter, also called "monomer having a nonreactive functional group) that can be copolymerized with a monomer having the specific functional group can be used.

Specific examples of this monomer include an acrylic acid ester compound, a methacrylic acid ester compound, a maleimide compound, an acrylamide compound, acrylonitrile, maleic anhydride, a styrene compound, and a vinyl compound.

Specific examples of these monomers have already described in [Component (B-1)].

Although the method for obtaining the specific (co) polymer 2 used for the cured-film formation composition of the present embodiment is not limited to a particular method, the specific (co)polymer 2 can be obtained, for example, by subjecting the monomer having the specific functional group, the monomer having the nonreactive functional group if desired, and a polymerization initiator or the like to polymerization reaction in a solvent in which they coexist at a temperature of 50° C. to 110° C. The solvent used herein is not limited as long as the solvent can dissolve the monomer having the specific functional group, the monomer having the nonreactive functional group used if desired, and a polymerization initiator or the like. Specific examples thereof include solvents described in [Solvent] described below.

The specific (co)polymer 2 thus obtained is generally in a state of a solution being dissolved in the solvent.

A solution of the specific (co)polymer 2 obtained as described above is poured into diethyl ether, water, or the like with stirring and the specific (co)polymer 2 is reprecipitated. The precipitate thus obtained is filtered and washed, and then is dried at room temperature or dried by heating under atmospheric pressure or reduced pressure. Thus, a powder of the specific (co)polymer 2 can be prepared. By this operation, the polymerization initiator and an unreacted monomer that coexist with the specific (co)polymer 2 can be removed, and consequently, a powder of the purified specific (co)polymer 2 can be obtained. If the specific (co)polymer 2 cannot be sufficiently purified by one operation, the obtained powder may be redissolved in a solvent, followed by repeating the operation described above.

In the cured-film formation composition of the present embodiment, the powder of the specific (co)polymer 2 may be used as such, or the powder may be used in a state of a solution being redissolved in a solvent described below.

In the present embodiment, the polymer of the component (B-2) may be a mixture of a plurality of the specific (co)polymers 2.

The weight-average molecular weight of this polymer is 1000 to 500000, preferably 1000 to 200000, more preferably 1000 to 100000, and further preferably 2000 to 50000.

These polymers may be used singly or in combination of two or more of them.

The melamine formaldehyde resin of the component (B-3) is a resin that is obtained by polycondensation between melamine and formaldehyde, and is a resin of Formula:

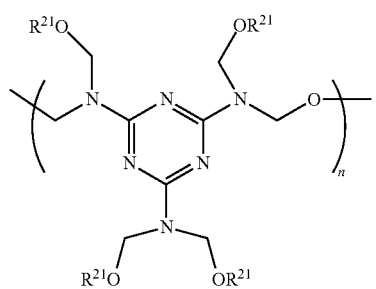

In the Formula, $R^{21}$ is a hydrogen atom or a $C_{1-4}$ alkyl group.

In the melamine formaldehyde resin of the component (B-3), a methylol group generated in the polycondensation between melamine and formaldehyde is preferably alkylated from the viewpoint of preservation stability.

Although the method for obtaining the melamine formaldehyde resin of the component (B-3) is not limited to a particular method, the melamine formaldehyde resin is synthesized generally by mixing melamine and formaldehyde, making this mixture weakly alkaline with sodium carbonate, ammonia, or the like, and then heating the mixture at 60° C. to 100° C. By additional reaction with alcohol, the methylol group can be alkoxylated.

The melamine formaldehyde resin of the component (B-3) has a weight-average molecular weight of preferably 250 to 5000, more preferably 300 to 4000, and further preferably 350 to 3500. An excessively high weight-average molecular weight exceeding 5000 may reduce the solubility in solvent, so that the handling property may deteriorate, and an excessively low weight-average molecular weight below 250 may cause insufficient curing during heat curing, so that the effect of improving the solvent resistance and the heat resistance cannot be sufficiently obtained in some cases.

In the embodiment of the present invention, the melamine formaldehyde resin of the component (B-3) may be used in a form of liquid or in a form of solution in which the purified liquid is redissolved in a solvent described below.

In the embodiment of the present invention, the component (B) may be a mixture of a plurality of polymers selected from the components (B-1), (B-2), and (B-3).

The composition of the present invention contains a cross-linking agent as the component (C) as described above. This makes it possible to perform cross-linking reaction by thermal reaction using the cross-linking agent (C) inside the cured film obtained from the composition of the present invention before the photoreaction with the photo-aligning group of the compound of the component (A). Consequently, when the composition is used as an orientation material, the resistance to the polymerizable liquid crystal and the solvent thereof applied onto the orientation material can be improved.

[Component (C)]

The composition of the present invention contains a cross-linking agent as the component (C).

More specifically, the component (C) is a cross-linking agent that reacts with the component (A) or the component (B) or reacts with both of them, and also reacts at a temperature lower than the sublimation temperature of the component (A). When the cured-film formation composition of the present embodiment contains an adhesive component as the component (D), the component (C) can react also with the component (D). At a temperature lower than the sublimation temperature of the component (A), the component (C) binds to at least one substituent selected from the group consisting a hydroxy group, a carboxy group, an amino group, and an alkoxysilyl group of a compound that is the component (A), at least one substituent selected from the group consisting of a hydroxy group, a carboxy group, an amino group, and an alkoxysilyl group contained in the component (B), and a hydroxy group of a compound that is the component (D). Consequently, as described below, it is possible to prevent the component (A) from sublimating when the component (A), the component (B), and the component (D) react with the cross-linking agent that is the component (C). Thus, the composition of the present invention can form an orientation material having high photoreaction efficiency as a cured film as described above.

Examples of the cross-linking agent that is the component (C) include an epoxy compound, a methylol compound, and an isocyanate compound, and the methylol compound is preferred.

Specific examples of the methylol compound include compounds such as alkoxymethylated glycoluril, alkoxymethylated benzoguanamine, and alkoxymethylated melamine.

Specific examples of the alkoxymethylated glycoluril include 1,3,4,6-tetrakis(methoxymethyl)glycoluril, 1,3,4,6-tetrakis(butoxymethyl)glycoluril, 1,3,4,6-tetrakis(hydroxymethyl)glycoluril, 1,3-bis(hydroxymethyl)urea, 1,1,3,3-tetrakis(butoxymethyl)urea, 1,1,3,3-tetrakis(methoxymethyl)urea, 1,3-bis(hydroxymethyl)-4,5-dihydroxy-2-imidazolinone, and 1,3-bis(methoxymethyl)-4,5-dimethoxy-2-imidazolinone. Examples of the commercially available product thereof include: compounds such as glycoluril compounds (trade name: Cymel (registered trademark) 1170, Powderlink (registered trademark) 1174), a methylated urea resin (trade name: UFR (registered trademark) 65), and butylated urea resins (trade name: UFR (registered trademark) 300, U-VAN10S60, U-VAN10R, U-VAN11HV) manufactured by Mitsui Cytec Ltd.; and urea/formaldehyde-based resins (trade name: Beckamine (registered trademark) J-300S, P-955, N; highly condensed-type) manufactured by Dainihon Ink & Chemicals Inc.

Specific examples of the alkoxymethylated benzoguanamine include tetramethoxymethyl benzoguanamine. Examples of commercially available products thereof include a product (trade name: Cymel (registered trademark) 1123) manufactured by Mitsui Cytec Ltd. and products (trade name: NIKALAC (registered trademark) BX-4000, BX-37, BL-60, BX-55H) manufactured by Sanwa Chemical Co., Ltd.

Specific examples of the alkoxymethylated melamine include hexamethoxymethyl melamine. Examples of commercially available products thereof include methoxymethyl-type melamine compounds (trade name: Cymel (registered trademark) 300, 301, 303, 350) and butoxymethyl-type melamine compounds (trade name: Mycoat (registered trademark) 506, 508) manufactured by Mitsui Cytec Ltd., and methoxymethyl-type melamine compounds (trade name: NIKALAC (registered trademark) MW-30, MW-22, MW-11, MS-001, MX-002, MX-730, MX-750, MX-035) and butoxymethyl-type melamine compounds (trade name: NIKALAC (registered trademark) MX-45, MX-410, MX-302) manufactured by Sanwa Chemical Co., Ltd.

The component (C) may also be a compound obtained by condensing a melamine compound, a urea compound, a glycoluril compound, or a benzoguanamine compound in which a hydrogen atom of an amino group is substituted with a methylol group or an alkoxymethyl group. Examples thereof include a high-molecular-weight compound produced from a melamine compound and a benzoguanamine compound described in U.S. Pat. No. 6,323,310. Examples of commercially available products of the melamine compound include Cymel (registered trademark) 303 (trade name; manufactured by Mitsui Cytec Ltd.), and examples of commercially available products of the benzoguanamine compound include Cymel (registered trademark) 1123 (trade name; manufactured by Mitsui Cytec Ltd.).

Furthermore, as the component (C), it is also possible to use a polymer produced by using an acrylamide compound or a methacrylamide compound that is substituted with a hydroxymethyl group or an alkoxymethyl group such as N-hydroxymethylacrylamide, N-methoxymethylmethacrylamide, N-ethoxymethylacrylamide, and N-butoxymethylmethacrylamide. In this case, when the component (B) is the component (B-2), the component (C) may be the same as the component (B-2).

Examples of the polymer include a poly(N-butoxymethylacrylamide), a copolymer of N-butoxymethylacrylamide and styrene, a copolymer of N-hydroxymethylmethacrylamide and methyl methacrylate, a copolymer of N-ethoxymethylmethacrylamide and benzyl methacrylate, and a copolymer of N-butoxymethylacrylamide, benzyl methacrylate, and 2-hydroxypropyl methacrylate. The weight-average molecular weight of the polymer is 1,000 to 500,000, preferably 2,000 to 200,000, more preferably 3,000 to 150,000, and still more preferably 3,000 to 50,000.

These cross-linking agents may be used singly or in combination of two or more of them.

The content of the cross-linking agent of the component (C) in composition of the present invention is preferably 10 parts by mass to 400 parts by mass, more preferably 15 parts by mass to 200 parts by mass, based on 100 parts by mass of the total amount of the compound that is the component (A) and the polymer of the component (B). When the content of the cross-linking agent is excessively low, the solvent resistance and heat resistance of the cured film obtained from the cured-film formation composition decrease, and the orientation sensitivity thereof during photo-alignment decreases. When the content of the cross-linking agent is excessively high, the photo-alignment properties and the preservation stability may deteriorate.

The composition of the present invention can contain a compound having a hydroxy group and an acrylic group other than the component (A), as the component (D) in addition to the component (A), the component (B), and the component (C). When the film of the present embodiment is used as an orientation material, the compound as the component (D) functions so as to enhance the adhesion between the film and a layer of a polymerizable liquid crystal formed and cured on the film. The following describes the component (D) contained in the composition of the present invention.

[Component (D)]

The component (D) contained in the composition of the present invention is a compound having a group that is thermally cross-linkable with the component (C) and an acrylic group. The component (D) is preferably a compound having a hydroxy group and an acrylic group other than the component (A).

When a cured film formed from the composition of the present invention containing the component (D) is used as an orientation material, so as to enhance the adhesion between the orientation material and the layer of the polymerizable liquid crystal, the polymerizable functional group of the polymerizable liquid crystal and a cross-linking reaction moiety of the orientation material can be linked by covalent bonding. Consequently, the retardation material of the present embodiment that is formed by laminating the polymerizable liquid crystal on the orientation material of the present embodiment can maintain excellent adhesion even under high-temperature and high-humidity conditions, and can have high durability against peeling or the like.

The content of the component (D) in the composition of the present invention is preferably 0.1 part by mass to 40 parts by mass, and more preferably 5 parts by mass to 35 parts by mass with respect to 100 parts by mass of the total amount of the compound that is the component (A) and the component (B). With the component (D) in a content of 0.1 part by mass or more, sufficient adhesion can be imparted to the cured film formed. However, when the content exceeds 40 parts by mass, the preservation stability of the cured-film formation composition may deteriorate.

In the composition of the present invention, the component (D) may be a mixture of a plurality of compounds of the component (D).

Preferred examples of the compound of the component (D) include compounds below. However, the compound of the component (D) is not limited to these exemplified compounds.

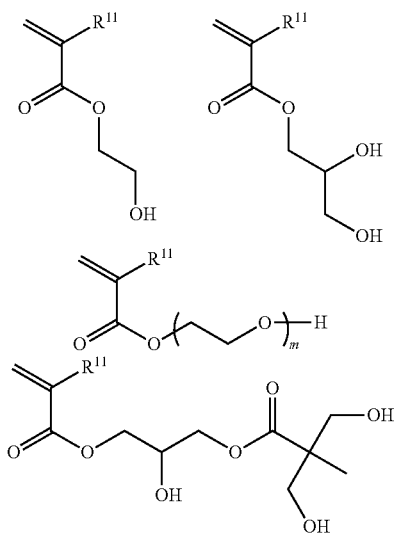

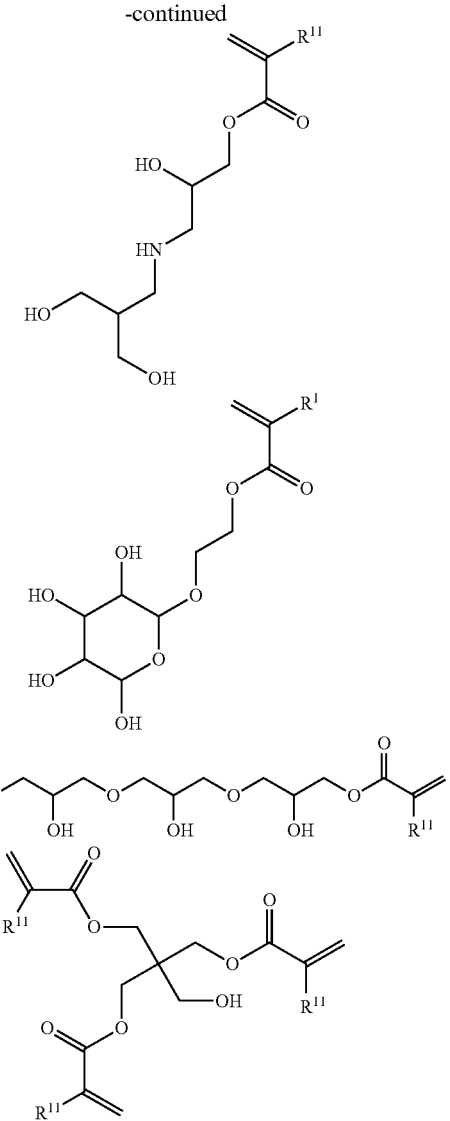

(In the Formulae, $R^{11}$ is a hydrogen atom or a methyl group; and m is an integer of 1 to 10.)

<Component (E)>

The cured-film formation composition of the present invention can contain the component (D) described above, and can further contain a cross-linking catalyst as a component (E) in addition to the component (A), the component (B), and the component (C).

The cross-linking catalyst that is the component (E) can be an acid or thermal acid generator, for example. This component (E) is effective in promoting heat-curing reaction in formation of the cured-film using the composition of the present invention.

When an acid or acid generator is used as the component (E), the component (E) is not limited as long as the component (E) is a sulfonic acid group-containing compound, hydrochloric acid or a salt thereof, or a compound that thermally decomposes to generate an acid during prebaking or postbaking, that is, a compound that thermally decomposes to generate an acid at a temperature of 80° C. to 250° C.

Examples of such a compound include hydrochloric acid; and sulfonic acid such as methanesulfonic acid, ethanesulfonic acid, propanesulfonic acid, butanesulfonic acid, pentanesulfonic acid, octanesulfonic acid, benzenesulfonic acid, p-toluenesulfonic acid, camphorsulfonic acid, trifluoromethanesulfonic acid, p-phenolsulfonic acid, 2-naphthalenesulfonic acid, mesitylenesulfonic acid, p-xylene-2-sulfonic acid, m-xylene-2-sulfonic acid, 4-ethylbenzenesulfonic acid, 1H,1H,2H,2H-perfluorooctanesulfonic acid, perfluoro(2-ethoxyethane)sulfonic acid, pentafluoroethanesulfonic acid, nonafluorobutane-1-sulfonic acid, and dodecylbenzenesulfonic acid, and a hydrate or a salt thereof.

Examples of the compound generating an acid by heat include bis(tosyloxy)ethane, bis(tosyloxy)propane, bis(tosyloxy)butane, p-nitrobenzyl tosylate, o-nitrobenzyl tosylate, 1,2,3-phenylene tris(methylsulfonate), p-toluenesulfonic acid pyridinium salt, p-toluenesulfonic acid morphonium salt, p-toluenesulfonic acid ethyl ester, p-toluenesulfonic acid propyl ester, p-toluenesulfonic acid butyl ester, p-toluenesulfonic acid isobutyl ester, p-toluenesulfonic acid methyl ester, p-toluenesulfonic acid phenethyl ester, cyanomethyl p-toluenesulfonate, 2,2,2-trifluoroethyl p-toluenesulfonate, 2-hydroxybutyl p- tosylate , N-ethyl-4-toluenesulfonamide, and the compounds of the Formulae [TAG-1] to [TAG-41].

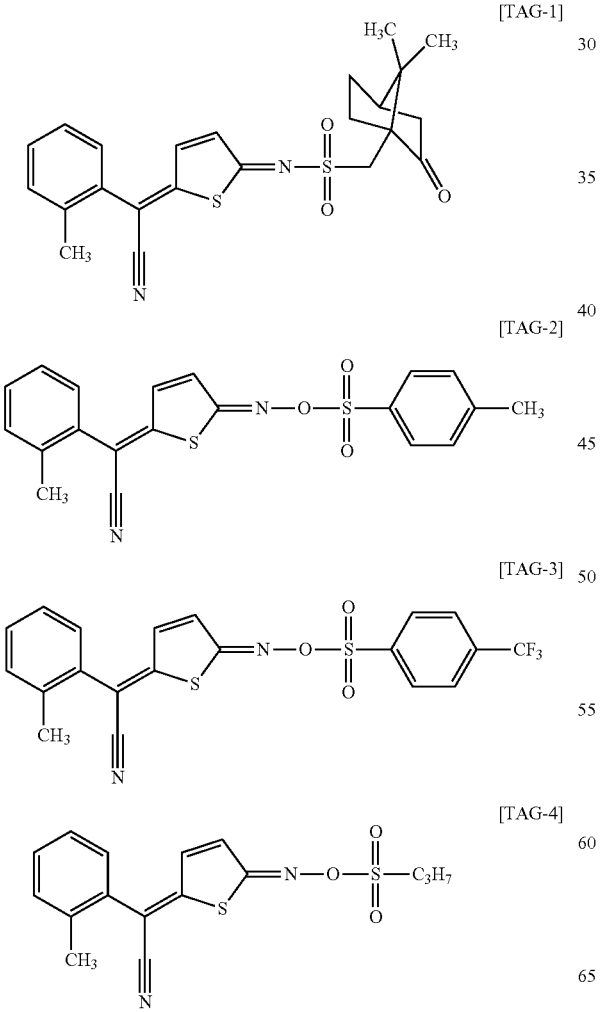

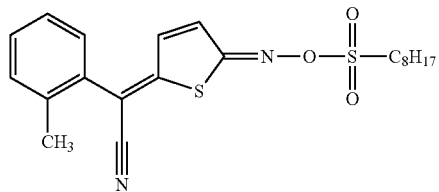

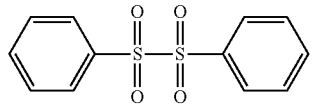

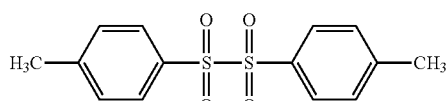

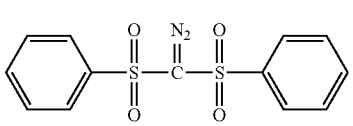

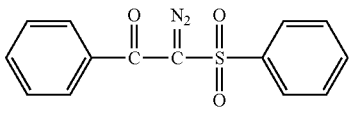

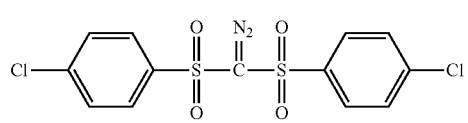

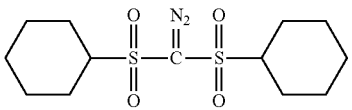

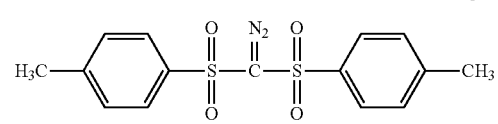

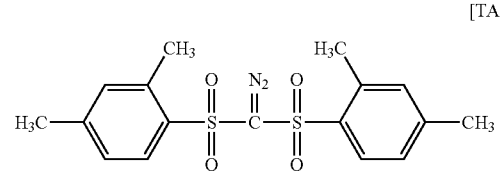

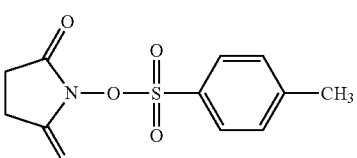

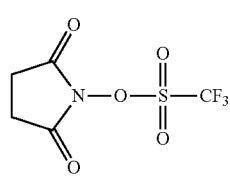

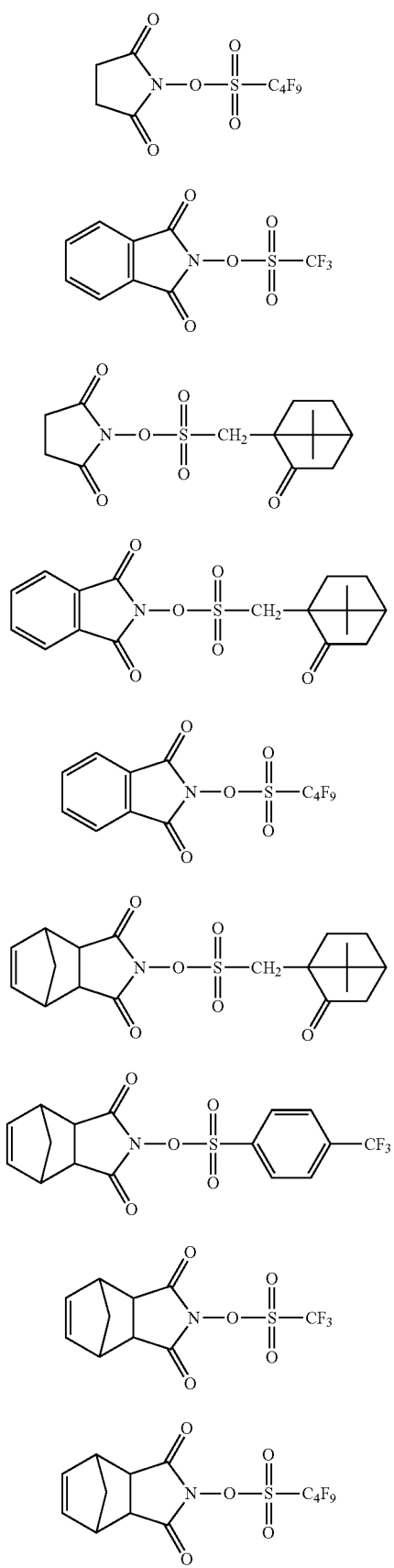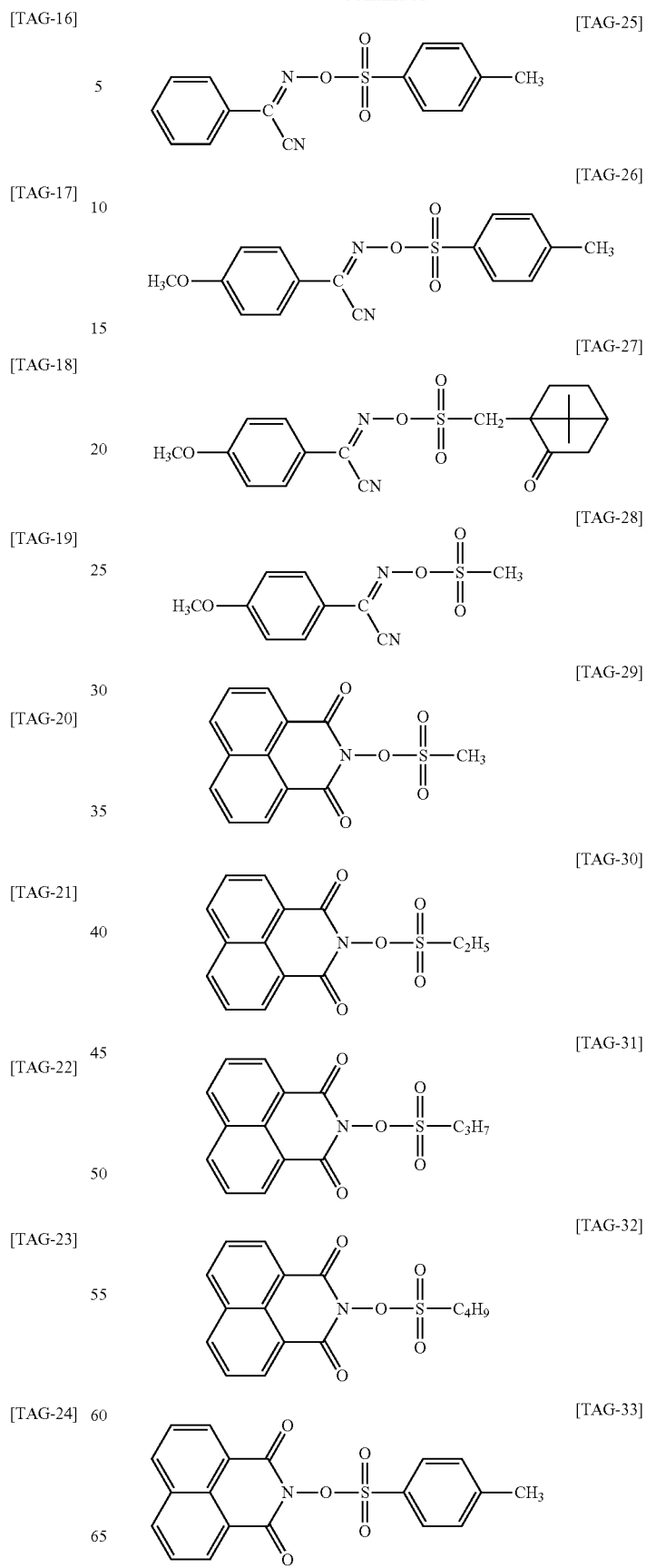

[TAG-34] 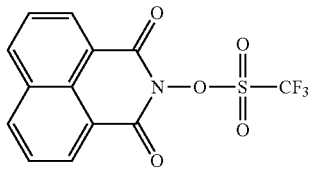

[TAG-35] 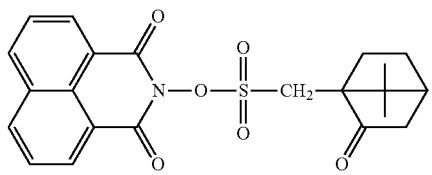

[TAG-36] 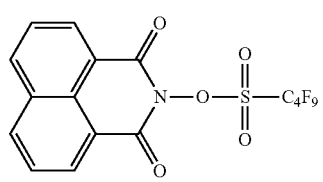

[TAG-37] 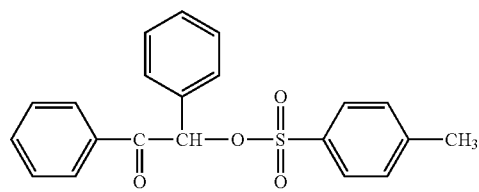

[TAG-38] 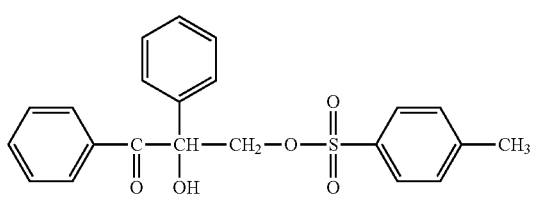

[TAG-39] 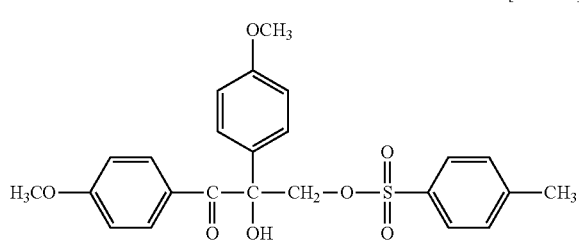

[TAG-40] 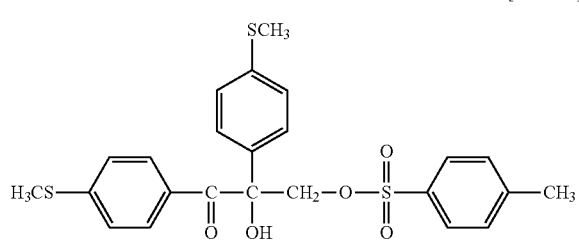

[TAG-41] 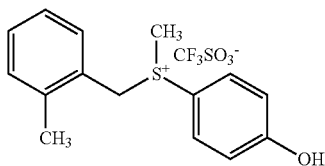

The content of the component (E) in the composition of the present invention is preferably 0.01 part by mass to 10 parts by mass, more preferably 0.05 part by mass to 8 parts by mass, and further preferably 0.1 part by mass to 6 parts by mass with respect to 100 parts by mass of the total amount of the compound that is the component (A) and the polymer that is the component (B). With the component (E) at a content of 0.01 part by mass or more, sufficient thermosetting properties and sufficient solvent resistance can be imparted to the composition, and high sensitivity to light exposure can also be imparted to the composition. Furthermore, by setting the content to 10 parts by mass or less, the preservation stability of the cured-film formation composition can be increased.

[Other Additives]

The composition of the present invention can contain other additives as long as the effects of the present invention are not impaired.

As one of the other additives, for example, a sensitizer can be contained. The sensitizer is effective in promoting photoreaction when a cured film of embodiments of the present invention is formed from the composition of the present invention.

Examples of the sensitizer include derivatives of benzophenone, anthracene, anthraquinone, and thioxanthone; and a nitrophenyl compound. Among them, N,N-diethylamino benzophenone that is a derivative of benzophenone and 2-nitrofluorene, 2-nitrofluorenone, 5-nitroacenaphthene, 4-nitrobiphenyl, 4-nitrocinnamic acid, 4-nitrostilbene, 4-nitrobenzophenone, and 5-nitroindole that are nitrophenyl compounds are particularly preferred.

These sensitizers are not limited to those described above. These sensitizers may be used singly or in combination of two or more compounds.

The proportion of the sensitizer used in the embodiments of the present invention is preferably 0.1 part by mass to 20 parts by mass, and more preferably 0.2 part by mass to 10 parts by mass with respect to 100 parts by mass of the component (A). When this proportion is excessively low, the effect as a sensitizer may not be sufficiently obtained, and when the proportion is excessively high, decrease of the transmittance and roughening of the cured film formed may occur.

Furthermore, the composition of the present invention can contain as other additives, as long as the effects of the present invention are not impaired, a silane coupling agent, a surfactant, a rheology adjusting agent, a pigment, a dye, a preservation stabilizer, an antifoamer, and an antioxidant, for example.

[Solvent]

The composition of the present invention is mainly used in a solution state in which the composition is dissolved in a solvent. The solvent, the structure thereof, and the like used herein are not limited as long as the solvent can dissolve the component (A), the component (B), and the component (C) and if necessary, the component (D), the component (E), and/or other additives and has such dissolving properties.

Specific examples of the solvent include ethylene glycol monomethyl ether, ethylene glycol monoethyl ether, methylcellosolve acetate, ethylcellosolve acetate, diethylene glycol monomethyl ether, diethylene glycol monoethyl ether, propylene glycol, propylene glycol monomethyl ether, propylene glycol monomethyl ether acetate, propylene glycol propyl ether acetate, toluene, xylene, methyl ethyl ketone, cyclopentanone, cyclohexanone, 2-butanone, 3-methyl-2-pentanone, 2-pentanone, 2-heptanone, γ-butyrolactone, ethyl 2-hydroxypropionate, ethyl 2-hydroxy-2-methylpropionate, ethyl ethoxyacetate, ethyl hydroxyacetate, methyl 2-hydroxy-3-methylbutanoate, methyl 3-methoxypropinoate, ethyl 3-methoxypropionate, ethyl 3-ethoxypropionate, methyl 3-ethoxypropionate, methyl pyruvate, ethyl pyruvate, ethyl acetate, butyl acetate, ethyl lactate, butyl lactate, N,N-dimethylformamide, N,N-dimethylacetamide, and N-methylpyrrolidone.

These solvents can be used singly or in combination of two or more of them. Among these solvents, propylene glycol monomethyl ether, propylene glycol monomethyl ether acetate, cyclohexanone, 2-heptanone, propylene glycol propyl ether, propylene glycol propyl ether acetate, ethyl lactate, butyl lactate, methyl 3-methoxypropionate, ethyl 3-methoxypropionate, ethyl 3-ethoxypropionate, and methyl 3-ethoxypropionate are preferred because of their excellent film-forming properties and high degree of safety.

<Preparation of Cured-Film Formation Composition>

The composition of the present invention is a cured-film formation composition that has photo-alignment properties and is thermosetting. As described above, the composition of the present invention contains a low-molecular alignment component that is the component (A); at least one polymer that is the component (B), selected from the component (B-1): a polymer that has at least one substituent selected from the group consisting of a hydroxy group, a carboxy group, an amino group, and an alkoxysilyl group, the component (B-2): a polymer that has a substituent capable of thermally reacting with the component (A) and is self-cross-linkable, and the component (B-3): a melamine formaldehyde resin; and a cross-linking agent that is the component (C). Furthermore, the composition may contain a compound having a hydroxy group and an acrylic group other than the component (A) as the component (D), and may contain a cross-linking catalyst as the component (E). Unless the effects of the present invention are impaired, the composition may contain other additives, and may further contain a solvent.

The blending ratio of the component (A) to the component (B) is preferably 5:95 to 60:40 in mass ratio. When the content of the compound (B) is excessively high, the liquid crystal alignment properties are likely to deteriorate. When the content is excessively low, the solvent resistance is reduced, whereby the alignment properties are likely to be degraded.

Preferred examples of the cured-film formation composition of the present invention are listed below.

[1]: A cured-film formation composition in which the blending ratio of the component (A) to the component (B) is 5:95 to 60:40 in mass ratio and that contains the component (C) at a content of 10 parts by mass to 400 parts by mass based on 100 parts by mass of the total amount of the component (A) and the component (B).

[1]: A cured-film formation composition in which the blending ratio of the component (A) to the component (B) is 5:95 to 60:40 in mass ratio and that contains the component (C) at a content of 10 parts by mass to 400 parts by mass based on 100 parts by mass of the total amount of the component (A) and the component (B), and a solvent.

[1]: A cured-film formation composition in which the blending ratio of the component (A) to the component (B) is 5:95 to 60:40 in mass ratio and that contains the component (C) at a content of 10 parts by mass to 400 parts by mass and the component (D) at a content of 0.1 part by mass to 40 parts by mass based on 100 parts by mass of the total amount of the component (A) and the component (B), and a solvent.

[1]: A cured-film formation composition in which the blending ratio of the component (A) to the component (B) is 5:95 to 60:40 in mass ratio and that contains the component (C) at a content of 0.1 part by mass to 40 parts by mass, the component (D) at a content of 10 parts by mass to 400 parts by mass, and the component (E) at a content of 0.01 part by mass to 10 parts by mass based on 100 parts by mass of the total amount of the component (A) and the component (B), and a solvent.

The blending proportion, a preparation method, and the like, when the composition of the present invention is used as a solution will be described below in detail.

The proportion of solid content in the composition of the present invention is, but not limited to as long as each component is uniformly dissolved in a solvent, 1% to 80% by mass, preferably 3% to 60% by mass, and more preferably 5% to 40% by mass. The solid content herein is a component remaining after excluding the solvent from all the components of the cured-film formation composition.

The preparation method of the cured-film formation composition of the present invention is not limited to a particular method. Examples of the preparation method include a method in which the component (A), the component (C), and further the component (D), and the component (E) are mixed in a solution of the component (B) dissolved in a solvent at predetermined proportions to make a homogeneous solution, or in a certain step of this preparation method, other additives are further added therein if necessary, and the resulting solution is mixed.

In the preparation of the cured-film formation composition of the present invention, a solution of the specific copolymer obtained by copolymerization reaction in the solvent can be used as such. In this case, for example, into a solution of the component (B), the component (A), the component (C), and further the component (D), the component (E), and the like, are mixed in the same manner described above, to make a homogeneous solution. At this time, a solvent may be further added thereto for the purpose of adjusting the concentration. In this case, the solvent used in the process of preparing the component (B) may be the same as or may be different from the solvent used for adjusting the concentration of the cured-film formation composition.

It is preferable that the solution of the cured-film formation composition thus prepared be used after being filtered with a filter having a pore diameter of about 0.2 μm.

<Cured Film, Orientation Material, and Retardation Material>

A cured film can be formed as follows: the solution of the composition of the present invention is applied onto a substrate (for example, a silicon/silicon dioxide coated substrate, a silicon nitride substrate, a substrate coated with a metal such as aluminum, molybdenum, and chromium, a glass substrate, a quartz substrate, and an ITO substrate) or a film (for example, a resin film such as a triacetylcellulose (TAC) film, a cycloolefin polymer film, a poly ethylene terephthalate film, and an acrylic film), and the like, by bar coating, rotation coating, flow coating, roll coating, slit coating, slit coating followed by rotation coating, inkjet coating, printing, or the like, to form a coating; and then the resultant coating is heated and dried on a hot plate or in an oven.

As a condition for the heating and drying, it is preferable that curing reaction proceed in such a manner that a component of an orientation material formed from the cured film is not eluted into a polymerizable liquid crystal solution applied onto the orientation material. For example, a heating temperature and a heating time that are appropriately selected from a temperature range of 60° C. to 200° C. and a time range of 0.4 minutes to 60 minutes are used. The heating temperature and the heating time are preferably 70° C. to 160° C. and 0.5 minute to 10 minutes.

The film thickness of the cured film formed of the composition of the present invention is 0.05 μm to 5 μm, for example, which can be appropriately selected in consideration of level differences and the optical and electrical properties of a substrate used.

When irradiated with polarized UV light, the cured film thus formed can function as an orientation material, that is, a member in which a compound having liquid crystallinity including polymerizable liquid crystals is aligned.

As a method for irradiation with polarized UV light, ultraviolet light to visible light having a wavelength of 150 nm to 450 nm are generally used, and the irradiation is performed by radiating linear polarized light in a vertical direction or an oblique direction at room temperature or in a heated state.

The orientation material formed of the composition of the present invention has solvent resistance and heat resistance. Thus, after a retardation substance including a polymerizable liquid crystal solution is applied onto the orientation material, the retardation substance is heated up to the phase transition temperature of the liquid crystal, whereby the retardation substance is transformed into a liquid crystal state to be aligned on the orientation material. The retardation substance thus aligned as desired is cured as such, whereby the retardation material including a layer having optical anisotropy can be formed.

As the retardation substance, for example, a liquid crystal monomer having a polymerizable group and a composition containing the liquid crystal monomer are used. When the substrate forming the orientation material is a film, the film having the retardation material of the present embodiment is useful as a retardation film. Some of such retardation substances for forming retardation materials are transformed into a liquid crystal state to be aligned in a state of horizontal alignment, cholesteric alignment, vertical alignment, hybrid alignment, or the like, and thus can be used differently depending on the respective retardation characteristics required.

When a patterned retardation material used for a 3D display is produced, a cured film that is formed of the composition of the present invention by the method described above is irradiated with polarized UV light in a direction of +45 degrees, for example, from a predetermined reference through a line-and-space pattern mask, and the cured film is then, after removing the mask, irradiated with polarized UV light in a direction of −45 degrees. Thus, an orientation material is obtained in which two kinds of liquid crystal alignment regions are formed and the directions of alignment control of liquid crystals in the regions are different. Subsequently, a retardation substance including a polymerizable liquid crystal solution is applied onto the orientation material, and is then heated up to the phase transition temperature of the liquid crystal. Thus, the retardation substance is transformed into a liquid crystal state. The polymerizable liquid crystal in a liquid crystal state is aligned on the orientation material in which two kinds of liquid crystal alignment regions are formed, and is aligned corresponding to the respective liquid crystal alignment regions. The retardation substance in which this alignment state is achieved is cured as such, whereby the alignment state described above is fixed. Thus, the patterned retardation material can be obtained in which two retardation regions having different retardation properties are regularly aligned each in plurality.

The orientation material formed from the composition of the present invention can be used as a liquid crystal alignment film for a liquid crystal display element. For example, two substrates having orientation materials of the present embodiment are used, and the substrates are stuck together with a spacer interposed therebetween so that the orientation materials on the respective substrates face each other. Subsequently, a liquid crystal is injected between the substrates, whereby a liquid crystal display element in which the liquid crystal is aligned can be produced. Thus, the composition of the present invention can be suitably used for producing various retardation materials (retardation films) or liquid crystal display elements.

EXAMPLES

The present embodiment will be described in further detail with reference to examples below.

[Composition Components and Abbreviations thereof used in Examples, etc.]

The composition components used in Examples and Comparative Examples below are as follows.

<Compound Having Photo-Aligning Group and Hydroxy Group>

CIN1: 4-(6-hydroxyhexyloxy)cinnamic acid methyl ester

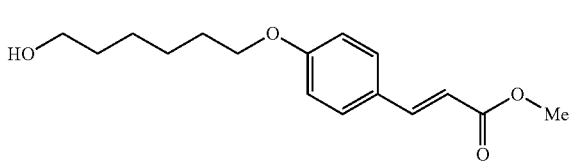 [SMILES: COC(=O)/C=C/c1ccc(OCCCCCCO)cc1]

CIN11: 4-[4-(6-hydroxyhexyloxy)benzoyl]cinnamic acid tertiary butyl ester

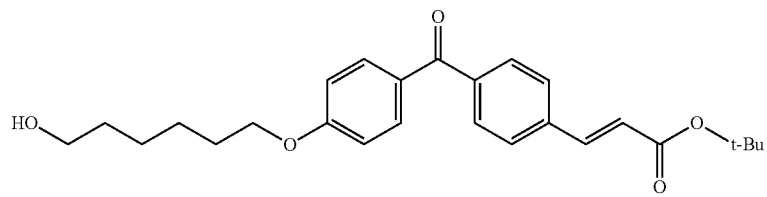 [SMILES: CC(C)(C)OC(=O)/C=C/c1ccc(C(=O)c2ccc(OCCCCCCO)cc2)cc1]

<Polymer of Component (B)>

PEPO: polyester polyol polymer (adipic acid/diethylene glycol copolymer having a structural unit below) (molecular weight 4,800)

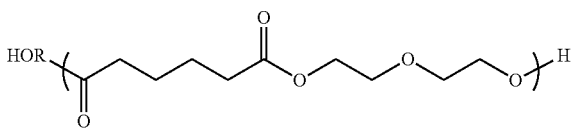

(In the Formula, R is alkylene.)

<Cross-Linking Agent>

HMM: melamine cross-linking agent of the structural formula below:

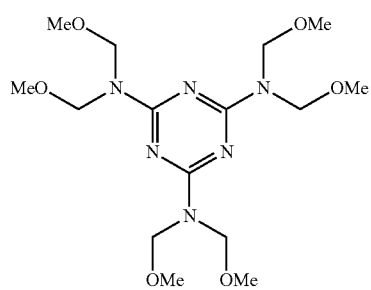 [SMILES: COCN(COC)c1nc(N(COC)COC)nc(N(COC)COC)n1]

<Cross-Linking Catalyst>

PTSA: p-toluenesulfonic acid

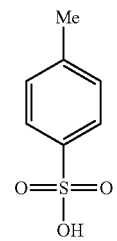

<Compound having Hydroxy Group and Acrylic Group>
D-1:

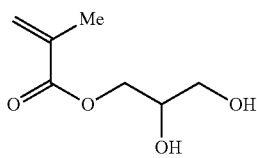

D-2: compound having a hydroxy group and an acrylic group of the structural formula below:

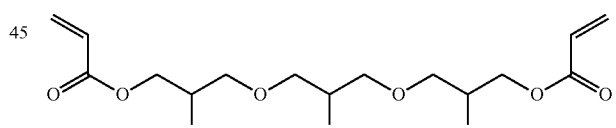

<Polymer Raw Material>
MAA: methacrylic acid
MMA: methyl methacrylate
HEMA: 2-hydroxyethyl methacrylate
BMAA: N-butoxy methyl acrylamide
AIBN: α,α'-azobisisobutyronitrile <Solvent>

Each of the cured-film formation compositions of Examples and Comparative Examples contain a solvent. As this solvent, propylene glycol monomethyl ether (PGME) was used.

<Measurement of Molecular Weight of Polymer>

The molecular weight of polyimide, polyamic acid, or acrylic polymers in Synthesis Examples was measured with a Shodex (registered trademark) room-temperature gel permeation chromatography (GPC) apparatus (GPC-101) and a Shodex column (KD-803, KD-805) as described below. The number-average molecular weight (hereinafter, called Mn) and the weight-average molecular weight (hereinafter, called Mw) below were expressed as values in terms of polystyrene.

Column temperature: 50° C.

Eluent: N,N-dimethylformamide (30 mmol/L of lithium bromide-hydrate (LiBr.H₂O), 30 mmol/L of phosphoric acid.anhydride crystal (o-phosphoric acid), and 10 mL/L of tetrahydrofuran (THF) as additives)

Flow rate: 1.0 mL/min

Standard samples for preparing calibration curves: TSK standard polyethylene oxide (molecular weight: about 900,000, 150,000, 100,000, 30,000) manufactured by Tosoh Corporation, and polyethylene glycol (molecular weight: about 12,000, 4,000, 1,000) manufactured by Polymer Laboratories Ltd.

<Measurement of ¹HNMR>

Apparatus: Fourier transformation superconducting nuclear magnetic resonance (FT-NMR) apparatus INOVA-400 (manufactured by Varian, Inc.) 400 MHz Solvent: deuterated dimethylsulfoxide (DMSO-$d_6$), deuterated chloroform (CDCl$_3$)

Reference material: tetramethylsilane (TMS)

EXAMPLES AND COMPARATIVE EXAMPLES

Synthesis Example 1

Synthesis of CIN11

Synthesis Example 1-1

Synthesis of CIN11-1 as Precursor of CIN11

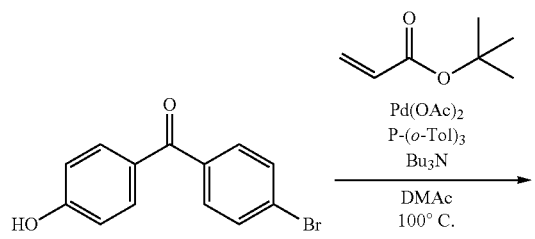

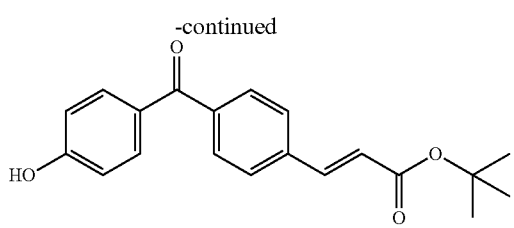

80.0 g of 4-bromo-4'-hydroxy benzophenone, 500 mL of N,N-dimethylacetamide, 55.4 g of tert-butyl acrylate, 160.2 g of tributylamine, 1.29 g of palladium acetate, 3.50 g of tri(o-tolyl)phosphine were put in a 1-L four-necked flask. This mixture was stirred while being heated at 100° C. After the reaction, the reaction system was poured into 2 L of ethyl acetate, and extraction was performed with a 1N-hydrochloric acid aqueous solution and a saturated brine. The organic phase thus extracted was dehydrated and dried over anhydrous magnesium sulfate, and then the anhydrous magnesium sulfate was filtered out. By using a rotary evaporator, the solvent was distilled off from the filtrate obtained, and thus 109.4 g of the target CIN11-1 (reddish-brown viscous substance) was obtained. The obtained CIN11-1 was used for the next reaction without being purified.

Synthesis Example 1-2

Synthesis of CIN11

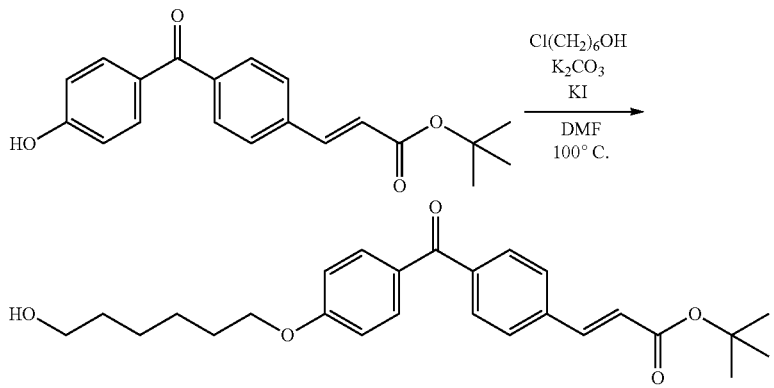

93.4 g of CIN11-1, 1 L of N,N-dimethylformamide, 39.3 g of 6-chloro-1-hexanol, 119.4 g of potassium carbonate, 4.8 g of potassium iodide were put in a 2-L four-necked flask. This mixture was stirred while being heated at 100° C. After the reaction, the reaction system was poured into 5 L of water and was neutralized with 1N-hydrochloric acid aqueous solution, and extraction was performed with ethyl acetate. The organic phase thus extracted was dehydrated and dried over anhydrous magnesium sulfate, and then the anhydrous magnesium sulfate was filtered out. By using a rotary evaporator, the solvent was distilled off from the filtrate obtained. The residue was recrystallized with isopropanol/hexane=1/10, and thus 113.8 g of CIN11 (ocher solid) was obtained. The results of the target substances measured for the ¹H-NMR is described below. Based on these results, it was confirmed that the obtained solid was the target CIN11.

¹H NMR (400 MHz, [D₆]-DMSO): δ7.86-7.88 (d, 2H), 7.73-7.75 (d, 2H), 7.69-7.71 (d, 2H), 7.62-7.66 (d, 1H), 7.08-7.10 (d, 2H), 6.65-6.69 (d, 1H), 4.35-4.37 (t, 1H), 4.06-4.09 (t, 2H), 3.37-3.42 (q, 2H), 1.73-1.77 (m, 2H), 1.50 (s, 9H), 1.37-1.46 (m, 6H)

Polymerization Example 1

3.5 g of MAA, 7.0 g of MMA, 7.0 g of HEMA, and 0.5 g of AIBN as a polymerization catalyst were dissolved in 53.9 g of PGME, and the resultant solution was caused to react at 70° C. for 20 hours to obtain an acrylic copolymer solution (solid-content concentration: 25% by mass) (P1). Mn and Mw of the obtained acrylic copolymer were 10,300 and 24,600, respectively.

Polymerization Example 2

100.0 g of MMA, 11.1 g of HEMA, and 5.6 g of AIBN as a polymerization catalyst were dissolved in 450.0 g of PGME, and the resultant solution was caused to react at 80° C. for 20 hours to obtain an acrylic copolymer solution (solid-content concentration: 20% by mass) (P2). Mn and Mw of the obtained acrylic copolymer were 4,200 and 7,600, respectively.

Polymerization Example 3

100.0 g of BMAA and 4.2 g of AIBN as a polymerization catalyst were dissolved in 193.5 g of PGME, and the resultant solution was caused to react at 90° C. for 20 hours to obtain an acrylic polymer solution (solid-content concentration: 35% by mass) (P3). Mn and Mw of the obtained acrylic copolymer were 2,700 and 3,900, respectively.

Examples 1 to 11, Comparative Example 1

Each of cured-film formation compositions of Examples and Comparative Example was prepared according to the formulations given in Table 1, and the alignment sensitivity, the pattern formability, and the transmittance of each thereof were evaluated.

TABLE 1

| | Component (A) (g) | Component (B) (g) | Component (C) (g) | Component (D) (g) | Component (E) (g) | Solvent (g) |
|---|---|---|---|---|---|---|
| Example 1 | CIN11 1.94 | P1 7.76 | HMM 1.94 | | PTSA 0.18 | PGME 88 |
| Example 2 | CIN1 + CIN11 0.97 + 0.97 | P1 7.76 | HMM 1.94 | | PTSA 0.18 | PGME 88 |
| Example 3 | CIN1 + CIN11 1.36 + 0.58 | P1 7.76 | HMM 1.94 | | PTSA 0.18 | PGME 88 |
| Example 4 | CIN11 1.67 | P1 6.69 | HMM 1.67 | D-1 0.84 | PTSA 0.15 | PGME 89 |
| Example 5 | CIN11 1.94 | PEPO 1.94 | HMM 1.94 | | PTSA 0.18 | PGME 94 |
| Example 6 | CIN11 1.67 | PEPO 1.67 | HMM 1.67 | D-1 0.84 | PTSA 0.15 | PGME 94 |
| Example 7 | CIN11 1.94 | | P3 11.1 | | PTSA 0.18 | PGME 87 |
| Example 8 | CIN11 1.45 | PEPO 1.45 | P3 8.32 | | PTSA 0.17 | PGME 84 |
| Example 9 | CIN11 1.94 | P2 9.71 | HMM 1.94 | | PTSA 0.17 | PGME 86 |
| Example 10 | CIN11 1.67 | P2 8.36 | HMM 1.67 | D-2 0.84 | PTSA 0.15 | PGME 94 |
| Example 11 | CIN11 1.46 | PEPO 1.46 | HMM 1.46 | D-1 1.46 | PTSA 0.13 | PGME 94 |
| Comparative Example 1 | CIN1 1.46 | PEPO 1.46 | HMM 1.46 | D-1 1.46 | PTSA 0.13 | PGME 94 |

[Evaluation of Alignment Sensitivity]

Each of the cured-film formation compositions of Examples and Comparative Examples was applied onto a TAC film with a bar coater, and then was heated and dried at 110° C. for 120 seconds in a heat circulation oven to form a cured film. The cured film was vertically irradiated with linear polarized light of 313 nm to form an orientation material. A polymerizable liquid crystal solution for horizontal alignment was applied onto the orientation material on a substrate with a bar coater, and then was prebaked on a hot plate at 70° C. for 60 seconds to form a coating having a film thickness of 1.0 µm. This coating on the substrate was exposed at 300 mJ/cm$^2$ to prepare a retardation material. The prepared retardation material on the substrate was sandwiched between a pair of polarizing plates, and the emergence of retardation properties in the retardation material was observed. The exposure amount of polarized UV light that was required for the orientation material to exhibit liquid crystal alignment properties was determined to be the alignment sensitivity. The evaluation results will be listed in Table 2 below.

[Evaluation of Pattern Formability]

Each of the cured-film formation compositions of Examples and Comparative Examples was applied onto a TAC film with a bar coater, and then was heated and dried at 110° C. for 120 seconds in a heat circulation oven to form a cured film. This cured film was vertically irradiated with linear polarized light of 313 µm at 40 mJ/cm$^2$ through a line-and-space pattern mask of 350 µm. After the mask was removed, the substrate was rotated 90 degrees, and was then vertically irradiated with linear polarized light of 313 nm at 20 mJ/cm$^2$. Thus, an orientation material was obtained in which two kinds of liquid crystal alignment regions were formed and the directions of alignment control of liquid crystals in the regions were different by 90 degrees. A polymerizable liquid crystal solution for horizontal alignment was applied onto this orientation material on the substrate with a bar coater, and then was prebaked on a hot plate at 70° C. for 60 seconds to form a coating having a film thickness of 1.0 µm. This coating on the substrate was exposed at 300 mJ/cm$^2$ to prepare a patterned retardation material in which two kinds of regions having different retardation characteristics are regularly aligned. The patterned retardation material prepared on the substrate was observed with a polarizing microscope.

Those on which a retardation pattern was formed without alignment failure were evaluated as "○", and those on which alignment failure was observed were evaluated as "×". The evaluation results will be listed in Table 2 below.

[Evaluation of Light Transmittance (Transparency)]

Each of the cured-film formation compositions of Examples and Comparative Examples was applied onto a quartz substrate with a spin coater, and then the resultant film was baked by heating and drying at 110° C. for 120 seconds on a hot plate to form a cured film having a film thickness of 200 nm. The film thickness was measured with F20 manufactured by Filmetrics, Inc. The transmittance of this cured film to light having a wavelength of 400 nm was measured with an ultraviolet-visible spectrophotometer (SHIMADZU UV-2550 manufactured by Shimadzu Corporation).

[Evaluation Results]

The results of the evaluation performed are given in Table 2 as described above.

TABLE 2

|  | Alignment sensitivity (mJ/cm$^2$) | Pattern formation | Transmittance (%) |
|---|---|---|---|
| Example 1 | 10 | ○ | 100 |
| Example 2 | 10 | ○ | 100 |
| Example 3 | 10 | ○ | 100 |
| Example 4 | 10 | ○ | 100 |
| Example 5 | 10 | ○ | 100 |
| Example 6 | 10 | ○ | 100 |
| Example 7 | 10 | ○ | 100 |
| Example 8 | 10 | ○ | 100 |
| Example 9 | 10 | ○ | 100 |
| Example 10 | 10 | ○ | 100 |
| Example 11 | 10 | ○ | 100 |
| Comparative Example 1 | 30 | X | 100 |

In all of the orientation materials obtained by using the cured-film formation compositions of Examples 1 to 11, the exposure amount of polarized UV light required to have liquid-crystal alignment properties was 10 mJ/cm$^2$, which is a small value. Thus, these orientation materials exhibited better alignment sensitivity than that of Comparative Example.

The orientation materials obtained by using the cured-film formation compositions of Examples 1 to 11 exhibited good pattern formability in the same degree as the orientation material obtained by using the cured-film formation composition of Comparative Example. However, in Comparative Example 1, the pattern was formed by increasing the irradiation amount to be twice that of Examples.

The cured films obtained by using the cured-film formation compositions of Examples 1 to 11 exhibited a transmittance of 100% or nearly 100% with respect to a light having a wavelength of 400 nm. Thus, these cured films exhibited good light transmission properties in the same degree as the cured film obtained by using the cured-film formation composition of Comparative Example.

INDUSTRIAL APPLICABILITY

The cured-film formation composition according to the present invention is very useful as a liquid crystal alignment film for a liquid crystal display element or an orientation material for forming an optically anisotropic film that is provided inside or outside the liquid crystal display element, and is particularly suitable as a material for forming a patterned retardation material for a 3D display. Furthermore, the cured-film formation composition is suitable as a material for forming a cured film such as a protective film, a planarization film, and an insulation film in various displays such as a thin film transistor (TFT) liquid crystal display element and an organic EL element, particularly as a material for forming an interlayer insulation film of a TFT liquid crystal element, a protective film for a color filter, an insulation film of an organic EL element, or the like.

The invention claimed is:
1. A cured-film formation composition comprising:
a component (A) comprising a compound having:
  a photo-aligning group, and
  a group selected from the group consisting of a hydroxy group, a carboxy group, an amino group, and an alkoxysilyl group;
a component (B) comprising a polymer selected from the group consisting of:
  a component (B-1): a polymer that has a substituent selected from the group consisting of a hydroxy group, a carboxy group, an amino group, and an alkoxysilyl group,
  a component (B-2): a polymer that has a substituent capable of thermally reacting with the component (A) and is self-cross-linkable, and
  a component (B-3): a melamine formaldehyde resin; and
a component (C) that is a cross-linking agent, wherein when the component (B) is the component (B-2), the component (C) is optionally the same as the component (B-2),
wherein:
the component (A) contains a compound having a group represented by Formula [1] below as the photo-aligning group:

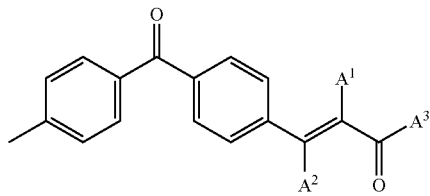

[1]

where:
  $A^1$ and $A^2$ are independently a hydrogen atom or a methyl group; and
  $A^3$ is a hydroxy group, a mercapto group, an amino group, a $C_{1-10}$ alkoxy group, a $C_{1-10}$ alkylthio group, a $C_{1-10}$ alkylamino group, a phenoxy group, a phenylthio group, a phenyl amino group, a biphenyl amino group, a phenyl group, or a biphenyl group; and
  hydrogen atoms on the phenylene group and on the phenyl group are independently and optionally substituted with a substituent selected from the group consisting of a $C_{1-10}$ alkyl group, a $C_{1-10}$ alkoxy group, a halogen atom, a cyano group, and a nitro group.

2. The cured-film formation composition according to claim 1, wherein the compound of the component (A) is a compound having a photo-aligning group of Formula [1] and a hydroxy group.

3. The cured-film formation composition according to claim 1, further comprising a component (D) that is a compound having a hydroxy group and an acrylic group, wherein the component (D) is not the same as the compound of the component (A).

4. The cured-film formation composition according to claim 1, further comprising a cross-linking catalyst (E).

5. An orientation material formed of the cured-film formation composition as claimed in claim 1.

6. A retardation material comprising a cured film that is obtained from the cured-film formation composition as claimed in claim 1.

7. A compound comprising:
a group represented by Formula [1] below; and
a group selected from the group consisting of a hydroxy group, a carboxy group, an amino group, and an alkoxysilyl group:

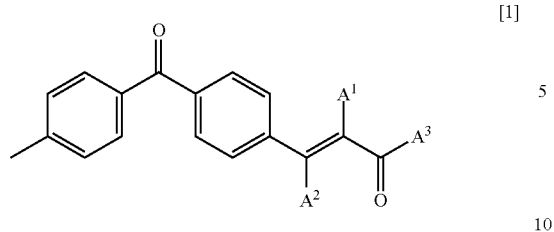

[1]

where:
- $A^1$ and $A^2$ are independently a hydrogen atom or a methyl group; and
- $A^3$ is a hydroxy group, a mercapto group, an amino group, a $C_{1-10}$ alkoxy group, a $C_{1-10}$ alkylthio group, a $C_{1-10}$ alkylamino group, a phenoxy group, a phenylthio group, a phenyl amino group, a biphenyl amino group, a phenyl group, or a biphenyl group;
- wherein hydrogen atoms on the phenylene group and on the phenyl group are independently and optionally substituted with at least one substituent selected from the group consisting of a $C_{1-10}$ alkyl group, a $C_{1-10}$ alkoxy group, a halogen atom, a cyano group, and a nitro group.

* * * * *